(12) United States Patent
Mori et al.

(10) Patent No.: US 8,988,517 B2
(45) Date of Patent: Mar. 24, 2015

(54) X-RAY IMAGING SYSTEM FOR MEDICAL USE

(75) Inventors: Harumichi Mori, Hamamatsu (JP); Ryuji Kyushima, Hamamatsu (JP); Kazuki Fujita, Hamamatsu (JP)

(73) Assignee: Hamamatsu Photonics K.K., Hamamatsu-shi, Shizuoka (JP)

( * ) Notice: Subject to any disclaimer, the term of this patent is extended or adjusted under 35 U.S.C. 154(b) by 1118 days.

(21) Appl. No.: 12/989,219

(22) PCT Filed: Apr. 22, 2009

(86) PCT No.: PCT/JP2009/058004
§ 371 (c)(1),
(2), (4) Date: Jan. 11, 2011

(87) PCT Pub. No.: WO2009/131151
PCT Pub. Date: Oct. 29, 2009

(65) Prior Publication Data
US 2011/0141255 A1 Jun. 16, 2011

(30) Foreign Application Priority Data
Apr. 24, 2008 (JP) .............................. P2008-114142

(51) Int. Cl.
H04N 7/18 (2006.01)
A61B 6/03 (2006.01)
A61B 6/14 (2006.01)
(Continued)

(52) U.S. Cl.
CPC . *A61B 6/032* (2013.01); *A61B 6/14* (2013.01); *A61B 6/4233* (2013.01); *G01T 1/2928* (2013.01); *H04N 5/2259* (2013.01); *H04N 5/32* (2013.01); *H04N 5/374* (2013.01);
(Continued)

(58) Field of Classification Search
CPC ....... A61B 1/041; A61B 1/00036; H04N 7/18
USPC ..................................................... 348/77–80
See application file for complete search history.

(56) References Cited

U.S. PATENT DOCUMENTS

| | | |
|---|---|---|
| 6,185,274 B1 | 2/2001 | Kinno et al. |
| 2006/0109361 A1 | 5/2006 | Sugiyama et al. |
| 2013/0201316 A1* | 8/2013 | Binder et al. ................... 348/77 |

FOREIGN PATENT DOCUMENTS

| | | |
|---|---|---|
| JP | 7-148163 | 6/1995 |
| JP | 9-122118 | 5/1997 |

(Continued)

*Primary Examiner* — Andy Rao
(74) *Attorney, Agent, or Firm* — Drinker Biddle & Reath LLP

(57) ABSTRACT

A solid-state image pickup apparatus 1A is formed such that M×N (where M<N and M and N are integers greater than or equal to 2) pixels are two-dimensionally arrayed in M rows and N columns, and has a photodetecting section 10A having a rectangular photosensitive surface whose longitudinal direction is the row direction. The solid-state image pickup apparatus 1A is supported rotatably by a rotation controlling section, and the rotation controlling section controls a rotation angle of the solid-state image pickup apparatus 1A such that the longitudinal direction of the photodetecting section 10A is made parallel to a moving direction B of the solid-state image pickup apparatus 1A in one imaging mode of the two imaging modes, and the longitudinal direction of the photodetecting section 10A is made perpendicular to the moving direction B of the solid-state image pickup apparatus 1A in the other imaging mode of the two imaging modes.

17 Claims, 18 Drawing Sheets

(51) Int. Cl.
  *A61B 6/00* (2006.01)
  *G01T 1/29* (2006.01)
  *H04N 5/225* (2006.01)
  *H04N 5/32* (2006.01)
  *H04N 5/374* (2011.01)
  *H04N 5/378* (2011.01)
(52) U.S. Cl.
  CPC ................. *H04N 5/378* (2013.01); *A61B 6/03* (2013.01); *A61B 6/4441* (2013.01)
  USPC .......................................................... 348/77

(56) References Cited

FOREIGN PATENT DOCUMENTS

| | | |
|---|---|---|
| JP | 11-318886 | 11/1999 |
| JP | 2007-144064 | 6/2007 |
| TW | 200818890 | 4/2008 |
| WO | 2006/109808 | 10/2006 |
| WO | 2007/046372 | 4/2007 |

\* cited by examiner

Fig.4
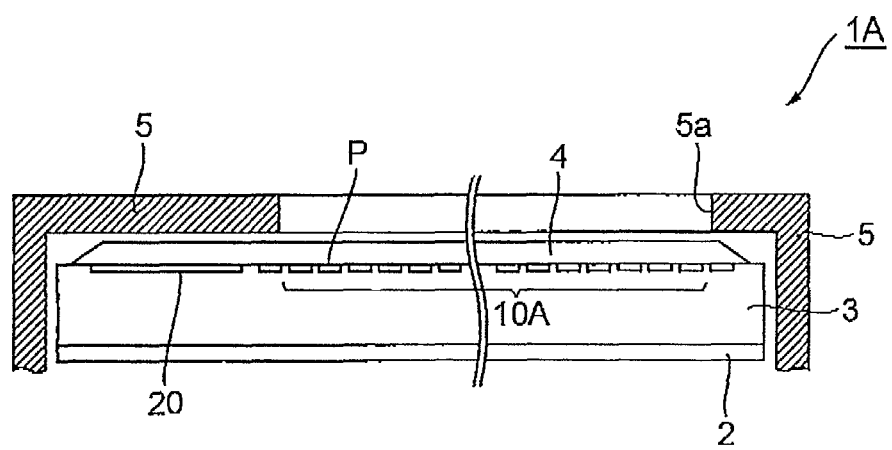
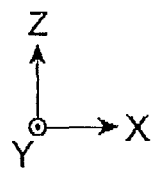

Fig.6
(a)
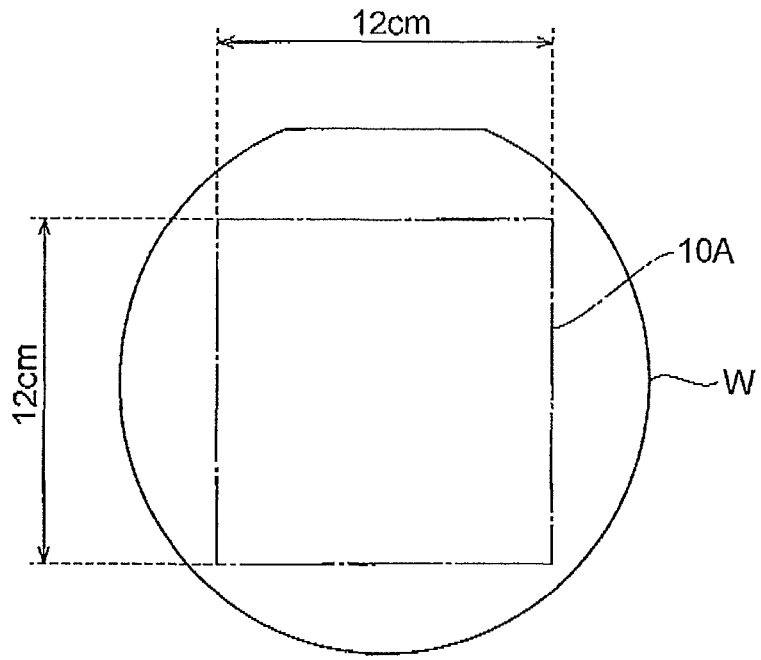
(b)
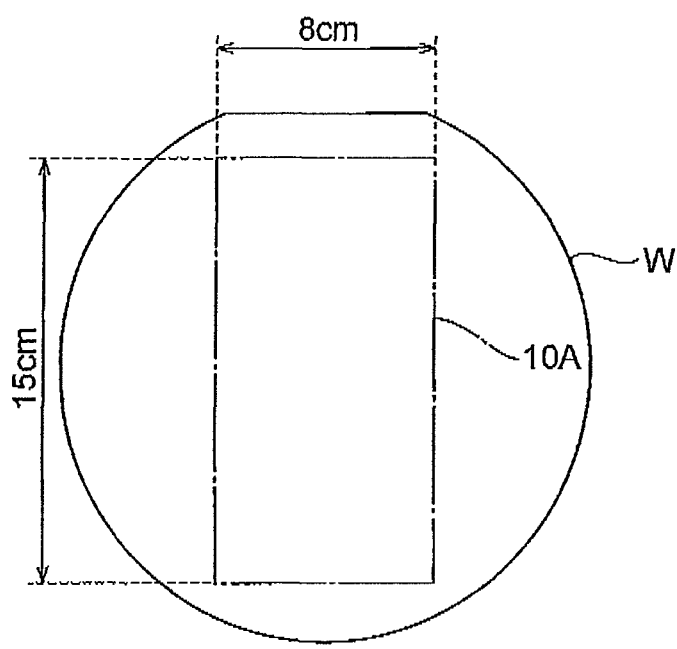

Fig.7
(a)
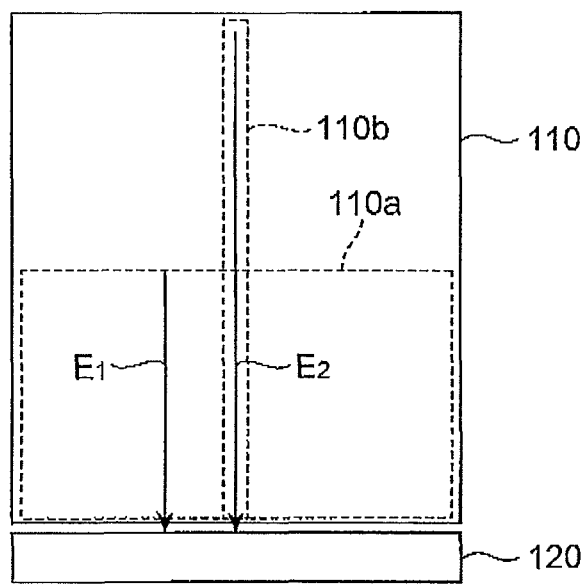
(b)
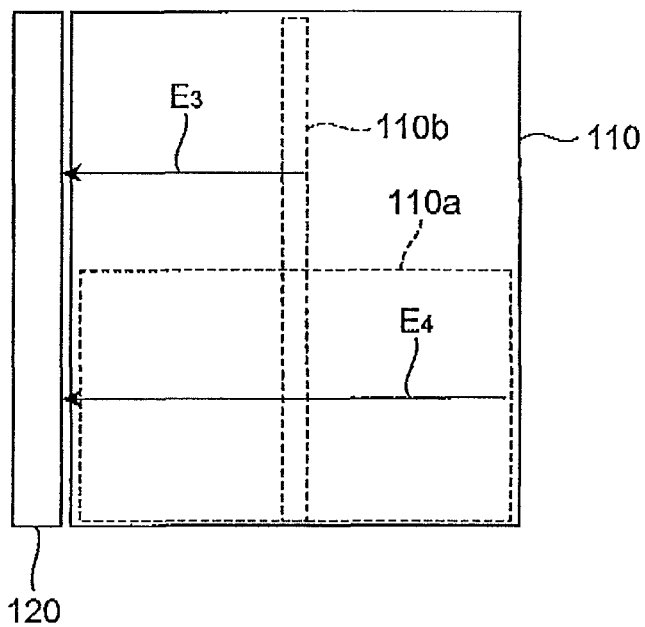

*Fig.8*
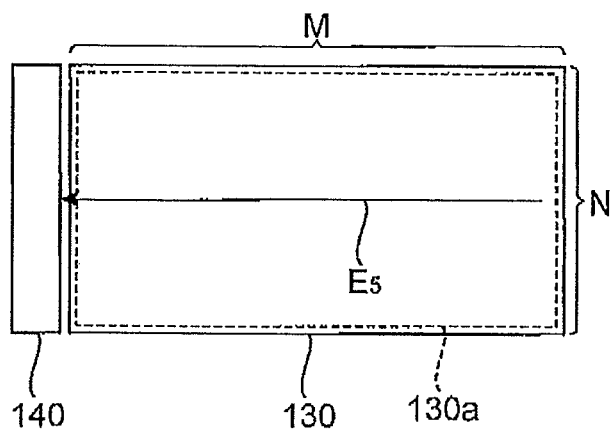
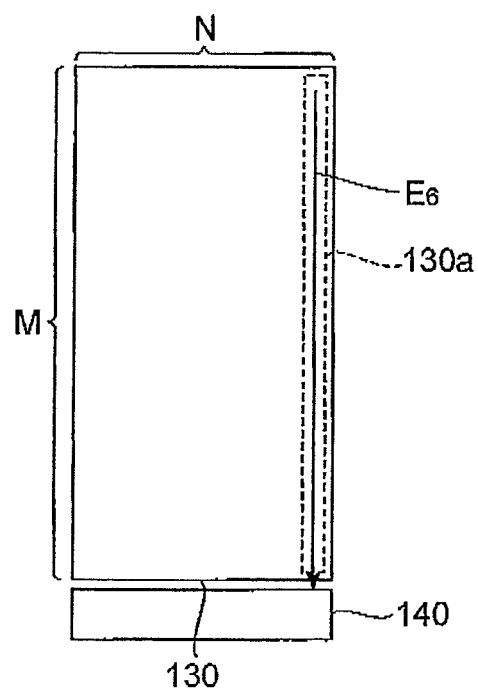

*Fig.9*
(a)
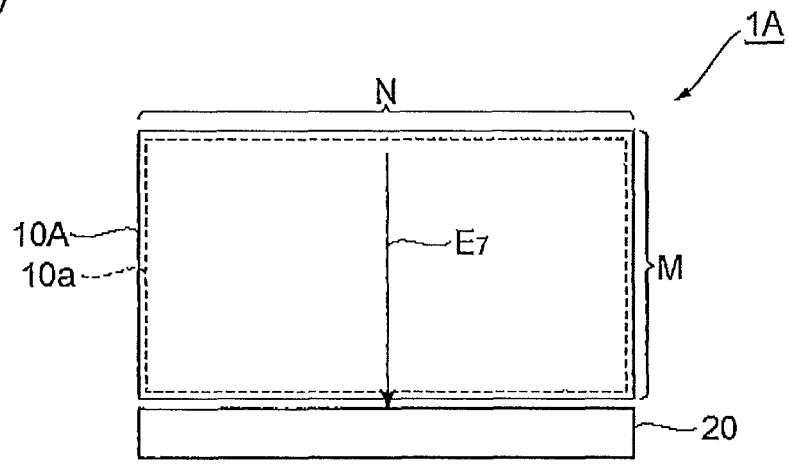
(b)
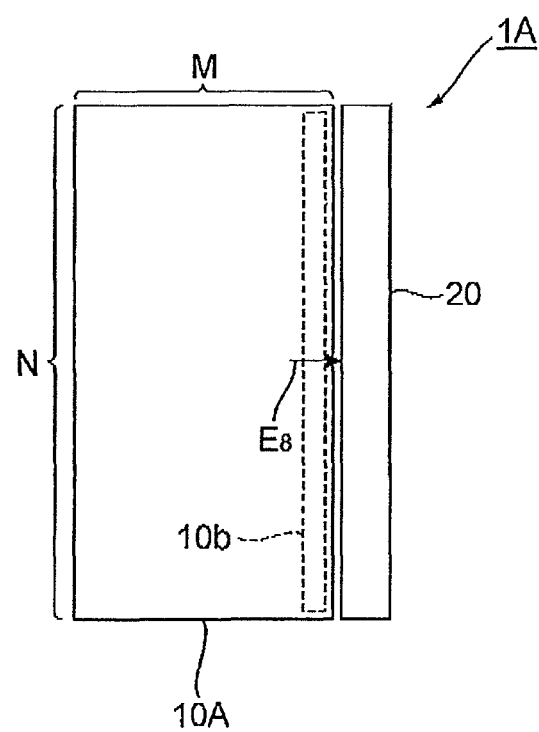

Fig.10
(a)
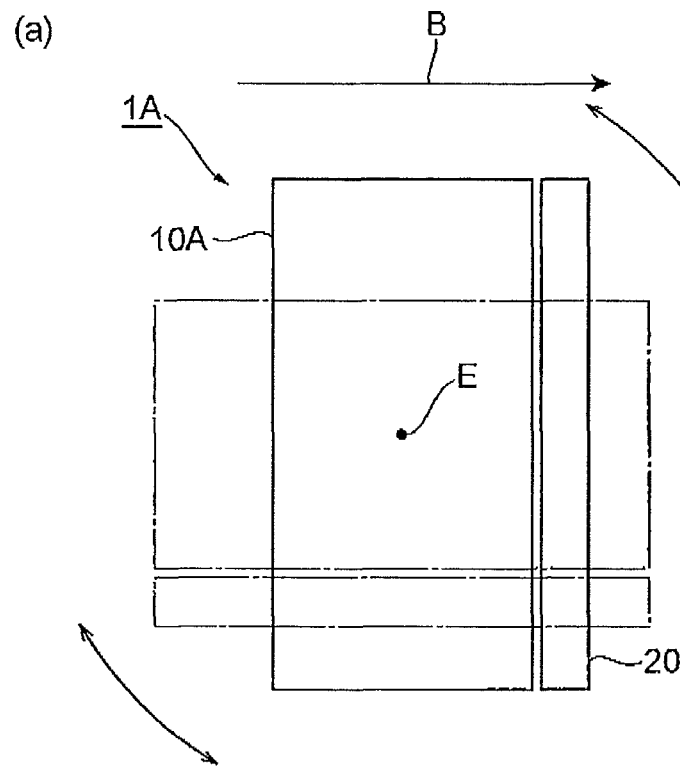
(b)
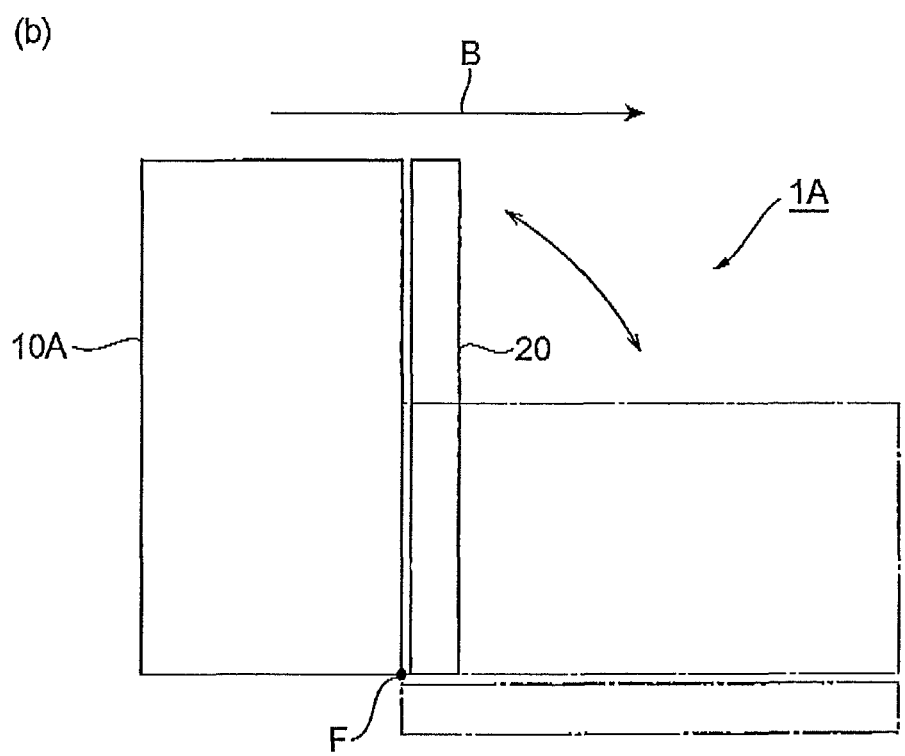

Fig.13
(a)
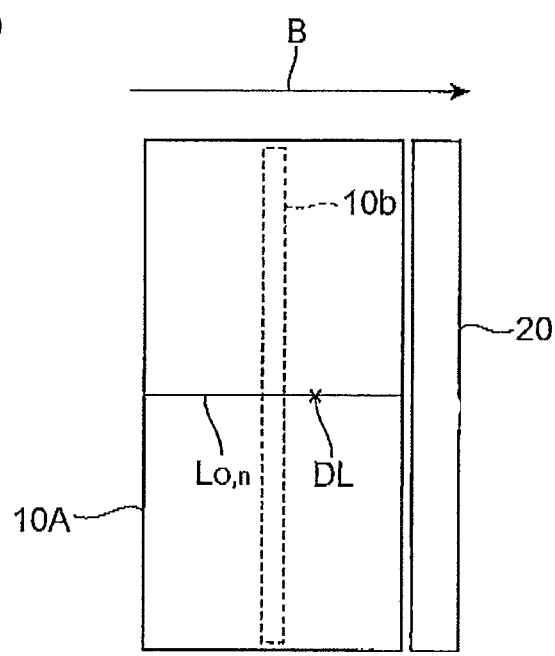
(b)
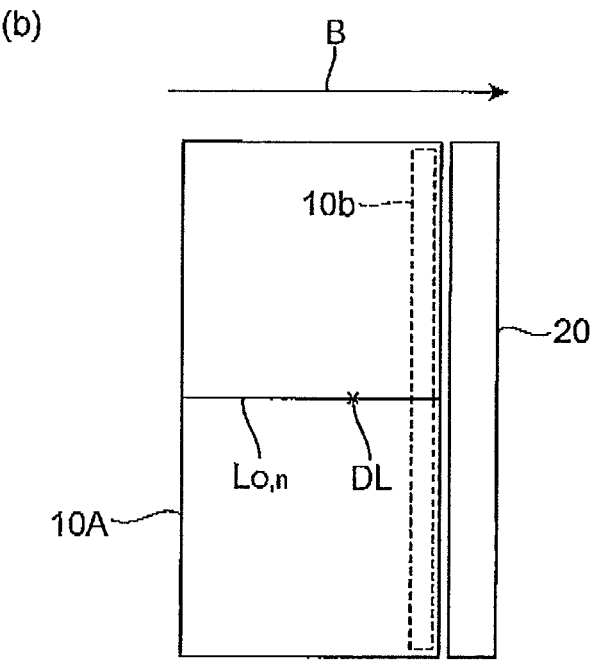

X-RAY IMAGING SYSTEM FOR MEDICAL USE

TECHNICAL FIELD

The present invention relates to an X-ray image pickup system for medical use.

BACKGROUND ART

In X-ray photography for medical use, in recent years, an X-ray imaging system using an X-ray image pickup apparatus in place of an X-ray sensitive film has been extensively used. Such an X-ray imaging system does not require development like that for an X-ray sensitive film, and is highly convenient in the point that it is possible to confirm an X-ray image in real time or the like, that also has superior points in aspects of data storage quality and data handling facilitation. In X-ray photography for dental diagnosis, also, such an X-ray imaging system has been used in various types of imaging modes, such as panoramic radiography, cephalometrical radiography, and CT scan.

In the case of a dental X-ray image pickup system, in some cases, the shape of an imaging area required for an X-ray image pickup apparatus differs according to various types of imaging modes described above. That is, a longitudinally sufficient width is required for an imaging area used for panoramic radiography or cephalometrical radiography. Further, a laterally sufficient width is required for an imaging area used for CT scan, and a certain measure of width is required therefor in a longitudinal direction as well. However, when a plurality of X-ray image pickup apparatuses meeting these requirements are made available, problems that the X-ray image pickup system is increased in size or it is necessary to exchange an X-ray image pickup apparatus at the time of changing an imaging mode, which takes time and labor, are brought about. Accordingly, it is preferable that one X-ray image pickup apparatus is capable of resolving these requirements for an imaging area.

For example, in Patent Document 1, there is disclosed a dental diagnosis X-ray image pickup apparatus equipped with an X-ray generator and an X-ray detector. In this X-ray image pickup apparatus, an X-ray is radiated via a narrow groove-like slit or a rectangular slit in order to be capable of selectively switching to generate an X-ray narrow slit beam and an X-ray broad beam. An X-ray narrow slit beam is used for panoramic radiography, cephalometrical radiography, or the like, and an X-ray broad beam is used for CT scan or the like. Then, in this Patent Document 1, there is described that both of an X-ray narrow slit beam passing through a narrow groove-like slit and an X-ray broad beam passing through a rectangular slit are taken as images by one solid-state image pickup element.

Further, as a solid-state image pickup apparatus used for such an X-ray image, pickup system for medical use, solid-state image pickup apparatuses using the CMOS technology are known, and a solid-state image pickup apparatus of a passive pixel sensor (PPS: Passive Pixel Sensor) system among those is known. A solid-state image pickup apparatus of a PPS system is equipped with a photodetecting section in which PPS-type pixels including photodiodes for generating charges according to incident light intensities are two-dimensionally arrayed in M rows and N columns, and charges generated in the photodiodes according to light incidence in the respective pixels are accumulated in capacitors in integrating circuits, and voltage values corresponding to the quantities of accumulated charges are output.

Generally, the respective output terminals of M pixels on each column are connected to an input terminal of an integrating circuit provided so as to correspond to the column via a readout wiring provided so as to correspond to the column. Then, the charges generated in the photodiodes in the respective pixels pass through the readout wiring corresponding to the column, and are input to the integrating circuit in series for each row of the first row to the M-th row, and voltage values corresponding to the quantities of charges are output.

CITATION LIST

Patent Literature

Patent Document 1: Pamphlet of International Publication No. 2006/109808

SUMMARY OF INVENTION

Technical Problem

As mentioned above, in the case of a dental X-ray image pickup system, in some cases, the shape of an imaging area required for a solid-state image pickup apparatus differs according to various types of imaging modes, such as panoramic radiography and CT scan, and it is preferable that these imaging modes can be realized by one solid-state image pickup apparatus. However, although X-ray beams in these imaging modes are taken as images by one solid-state image pickup apparatus in the configuration described in Patent Document 1, in order to set an imaging area for panoramic radiography with a longitudinally sufficient width and an imaging area for CT scan with a laterally sufficient width in one photosensitive surface, a broad photosensitive surface with both longitudinally and laterally sufficient widths is necessary. However, in some cases, due to the restrictions on the size of a semiconductor wafer serving as a material of a photodetecting section of a solid-state image pickup apparatus and the like, it is impossible to produce such a solid-state image pickup apparatus having a broad photosensitive surface.

The present invention has been achieved in order to solve the above-described problems, and an object of the present invention is, in an X-ray image pickup system for medical use having at least two imaging modes, to realize the two imaging modes by one solid-state image pickup apparatus and to suppress an increase in area required for a photosensitive surface of the solid-state image pickup apparatus.

Solution to Problem

An X-ray image pickup system for medical use according to the present invention, which has at least two imaging modes, the X-ray image pickup system for medical use comprising a solid-state image pickup apparatus which takes an X-ray image while moving around a jaw portion of a test subject, and in which the solid-state image pickup apparatus has a photodetecting section which is formed such that M×N (where M<N and M and N are integers greater than or equal to 2) pixels respectively including photodiodes are two-dimensionally arrayed in M rows and N columns, the photodetecting section has a rectangular photosensitive surface whose longitudinal direction is the row direction, N readout wirings which are installed on the respective columns, and connected to the photodiodes included in the pixels on corresponding columns via readout switches, a signal readout section which holds voltage values corresponding to quantities of charges input via the readout wirings, and outputs the holding voltage values in series, a controlling section which controls switching operations of the readout switches of the respective pixels, and controls outputting operations of voltage values in the signal readout section, to output the voltage values corresponding to the quantities of charges generated in the photodiodes of the respective pixels from the signal readout section, and a scintillator which generates a scintillation light according to an incident X-ray to convert the X-ray image into an optical image, and outputs the optical image to the photodetecting section, the X-ray image pickup system for medical use further comprises a rotation controlling section which supports the solid-state image pickup apparatus rotatably around an axis line vertical to the photosensitive surface, and controls a rotation angle of the solid-state image pickup apparatus such that the longitudinal direction of the photodetecting section is made parallel to a moving direction of the solid-state image pickup apparatus in one imaging mode of the two imaging modes, and the longitudinal direction of the photodetecting section is made perpendicular to the moving direction of the solid-state image pickup apparatus in the other imaging mode of the two imaging modes.

In the X-ray image pickup system for medical use according to the present invention, the photodetecting section of the solid-state image pickup apparatus has the rectangular photosensitive surface. Further, this solid-state image pickup apparatus is supported rotatably around the axis line vertical to the photosensitive surface by the rotation controlling section. Then, a rotation angle of the solid-state image pickup apparatus is controlled such that the longitudinal direction of the photodetecting section is made parallel to the moving direction of the solid-state image pickup apparatus in one imaging mode of the two imaging modes (for example, CT scan mode), and the longitudinal direction of the photodetecting section is made perpendicular to the moving direction of the solid-state image pickup apparatus in the other imaging mode (for example, panoramic radiography mode). With such a configuration, in the case where an imaging area whose longitudinal direction is the moving direction of the solid-state image pickup apparatus (for example, an imaging area for CT scan) is necessary and in the case where an imaging area whose longitudinal direction is the direction perpendicular to the moving direction of the solid-state image pickup apparatus (for example, an imaging area for panoramic radiography) is necessary, respectively, the longitudinal directions of the imaging areas and the longitudinal direction of the photodetecting section can be matched to one another. Accordingly, in accordance with the above-described X-ray image pickup system for medical use, it is possible to realize the two imaging modes by the one solid-state image pickup apparatus, and suppress an increase in area of the photosensitive surface necessary for setting the imaging areas of different shapes, which are necessary for the respective imaging modes in one photosensitive surface.

Further, in the X-ray image pickup system for medical use according to the present invention, the shape of the photosensitive surface of the solid-state image pickup apparatus in which the plurality of pixels are two-dimensionally arrayed in M rows and N columns is a rectangle whose longitudinal direction is the row direction, where M<N, that is, the number of columns of pixels is greater than the number of rows. Then, as described above, the longitudinal directions of the imaging areas in the respective imaging modes are matched to the longitudinal direction of the photosensitive surface. Further, in the X-ray image pickup system for medical use, in addition to such a configuration, readout wirings are installed on the respective columns, and therefore, the installing direction of the readout wirings and the short-side directions of the imaging areas are always matched to one another in the respective imaging modes. Accordingly, since it is possible to decrease the number of pixels (photodiodes) as targets from which charges are read out through the readout wirings in each frame in any one of the imaging modes, it is possible to further speed up its frame rate (the number of pieces of frame data to be output per unit time).

Further, the X-ray image pickup system for medical use may have the feature that a rotation center of the solid-state image pickup apparatus is located at one corner of the four corners of the rectangular photodetecting section, and the solid-state image pickup apparatus is rotated such that the one corner is located on the lower jaw side of the test subject in both of the two imaging modes. When the solid-state image pickup apparatus takes an X-ray image while moving around a jaw portion of a test subject, the lower jaw portion of the test subject is placed on a support table to fix the head position of the test subject in many cases, and in such a case, the standard for the position in height of the jaw portion of the test subject is to be the lower end of the jaw. According to the X-ray image pickup system for medical use, the heights of the lower ends of the photosensitive surface in the two imaging modes can be matched to one another at a height of the corner serving as a rotation center. Accordingly, it is possible to accurately match the heights of the photosensitive surface in the two imaging modes and the height of the jaw portion of the test subject.

Further, the X-ray image pickup system for medical use may have the feature that the controlling section outputs voltage values corresponding to the quantities of charges generated in the photodiodes of the M×N respective pixels in the photodetecting section from the signal readout section in one imaging mode, and the controlling section outputs voltage values corresponding to the quantities of charges generated in the photodiodes of the respective pixels included in a specific range of successive $M_1$ rows ($M_1$<M) in the photodetecting section from the signal readout section in the other imaging mode. With this feature, it is possible to favorably realize an imaging area with a width differing according to each of the respective imaging modes, for example, an imaging area in a shape slightly wider laterally in a CT scan mode, and an imaging area in an elongated shape whose longitudinal direction is the vertical direction in a panoramic radiography mode.

In this case, it is preferable that, in the other imaging mode, the controlling section sets a range of $M_1$ rows counted in order from the row closest to the signal readout section among the M rows in the photodetecting section as the specific range, and outputs voltage values corresponding to the quantities of charges generated in the photodiodes of the respective pixels in this specific range. With this, it is possible to reduce the probability of being incapable of reading out the specific range (i.e., the imaging area) in the case where a fault such as disconnection is caused in a readout wiring. Further, it is preferable that the solid-state image pickup apparatus further has disconnecting switches which are provided on the respective readout wirings between the specific range in the photodetecting section and the other range except for the specific range, and the controlling section closes the disconnecting switches in the one imaging mode, and opens the disconnecting switches in the other imaging mode. With this, it is possible to favorably carry out switching imaging areas corresponding to the respective imaging modes.

Further, it is preferable that, in the case where the controlling section outputs voltage values corresponding to the quantities of charges in the respective pixels included in the specific range in the other imaging mode from the signal readout section, the solid-state image pickup apparatus further has discharge means for discharging junction capacitance sections of the photodiodes of the respective pixels in the other range except for the specific range in the photodetecting section in the other imaging mode. With this, it is possible to easily discharge the charges accumulated in the photodiodes of the respective pixels included in the other range except for the specific range in the other imaging mode.

Further, the X-ray image pickup system for medical use may have the feature that, in, the other imaging mode, the controlling section reduces a readout pixel pitch in frame data based on a voltage value output from the signal readout section as compared to the one imaging mode, speeds up a frame rate, that is the number of pieces of frame data to be output per unit time, and increases gain, that is a ratio of an output voltage value to an amount of input charges in the signal readout section. With this feature, it is possible to perform the operations suitable for the respective imaging modes such as CT scan or panoramic radiography.

Further, it is preferable that, in the X-ray image pickup system for medical use, the one imaging mode is an imaging mode for carrying out CT scan in dental X-ray photography, and the other imaging mode is an imaging mode for carrying out panoramic radiography in dental X-ray photography.

Advantageous Effects of Invention

In accordance with the present invention, in an X-ray image pickup system for medical use having at least two imaging modes, it is possible to realize the two imaging modes by one solid-state image pickup apparatus and suppress an increase in area required for a photosensitive surface of the solid-state image pickup apparatus.

BRIEF DESCRIPTION OF DRAWINGS

FIG. 4 is a sectional side view of the solid-state image pickup apparatus 1A along line IV-IV of FIG. 3.

FIG. 5-($b$) is a diagram showing an angular position of the solid-state image pickup apparatus 1A in an imaging mode such as panoramic radiography or cephalometrical radiography (a second imaging mode) and an imaging area 10$b$ in the photodetecting section 10A.

FIG. 6-($a$) is a diagram showing the situation that a square panelization is performed onto a silicon wafer W for the photodetecting section 10A, and FIG. 6$b$) is a diagram showing the situation that a rectangular panelization is performed onto the silicon wafer W for the photodetecting section 10A.

FIG. 7-($a$) and FIG. 7-($b$) are diagrams showing charge readout methods in a conventional solid-state image pickup apparatus using a photodetecting section so as not to be rotated. FIG. 7-($a$) shows the case where a signal readout section 120 is arranged along the longitudinal direction of an imaging area 110$a$, and FIG. 7-($b$) shows the case where the signal readout section 120 is arranged along the longitudinal direction of an imaging area 110$b$.

FIG. 8-($a$) shows a first imaging mode in the case where a signal readout section 140 is arranged along the short-side direction of a photodetecting section 130, and FIG. 8-($b$) is a diagram showing respective charge readout methods in a second imaging mode.

FIG. 9 are diagram showing charge readout methods of the solid-state image pickup apparatus 1A according to a first embodiment.

FIGS. 10-($a$) and 10-($b$) are diagrams showing the situations of rotation of the photodetecting section 10A according to the positions of the rotation centers (an axis line C shown in FIG. 1) of the solid-state image pickup apparatus 1A. FIG. 10-($a$) shows the case where a center E of the photodetecting section 10A is set as a rotation center of the solid-state image pickup apparatus 1A, and FIG. 10-($b$) shows the case where one corner F among the four corners of the rectangular photodetecting section 10A is set as a rotation center of the solid-state image pickup apparatus 1A, to rotate the solid-state image pickup apparatus 1A such that the corner F is located below the other corners throughout the first imaging mode and the second imaging mode.

FIG. 13-($a$) and FIG. 13-($b$) are diagrams for explanation of advantages of arranging the imaging area 10$b$ in the second imaging mode so as to be close to a signal readout section 20.

DESCRIPTION OF EMBODIMENTS

Figure 1:
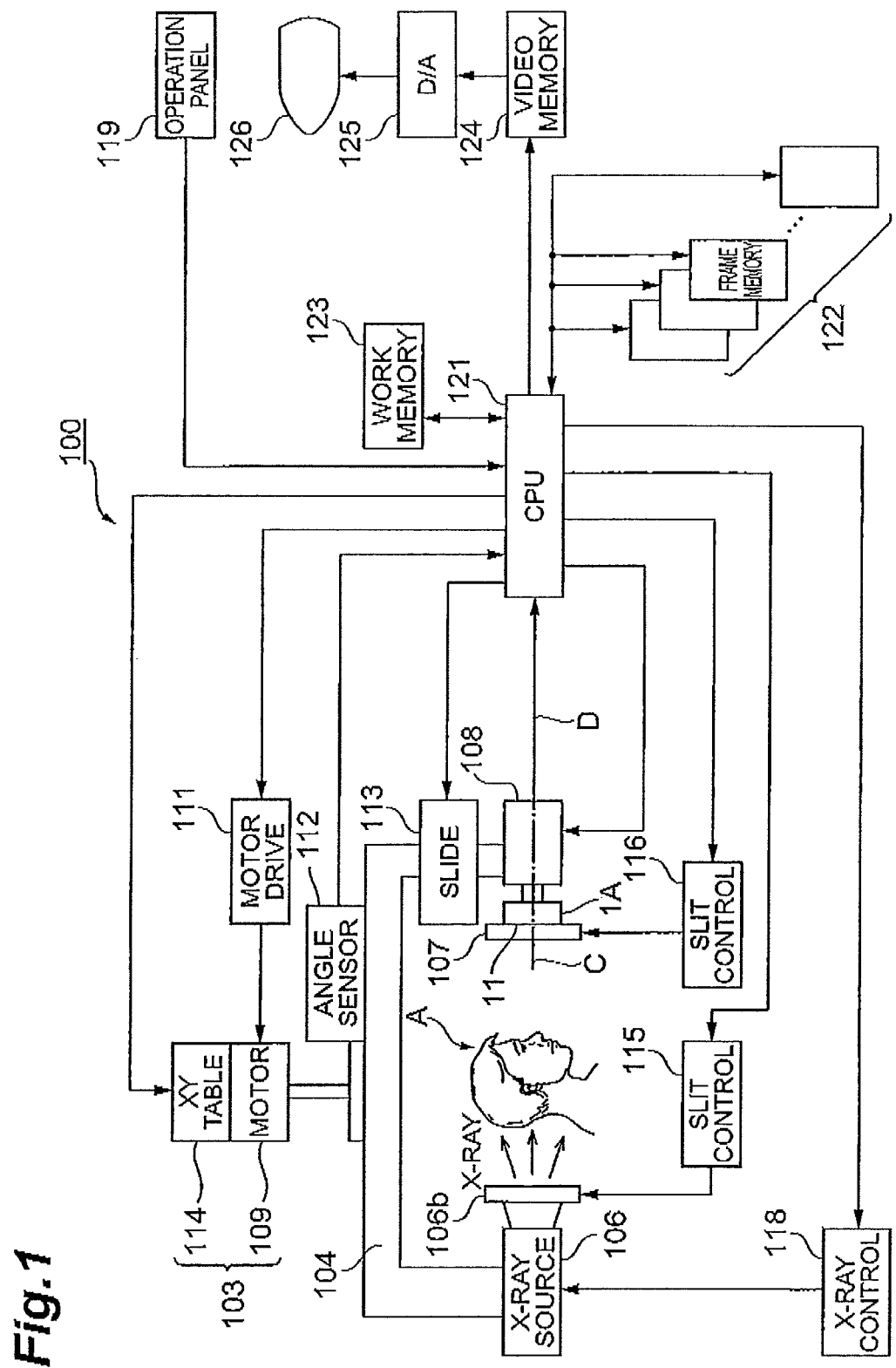
FIG. 1 is a configuration diagram of an X-ray image pickup system 100 according to a first embodiment.

Hereinafter, the best modes for carrying out the present invention will be described in detail with reference to the accompanying drawings. In addition, the same components are denoted by same reference numerals in descriptions of the drawings, and overlapping descriptions will be omitted.

FIG. 1 is a diagram showing the configuration of an X-ray image pickup system for medical use 100 as a first embodiment of the present invention. The X-ray image pickup system 100 of the present embodiment has imaging modes such as panoramic radiography, cephalometrical radiography, and CT scan mainly for dentistry medical treatment, and takes an X-ray image of a jaw portion of a test subject. The X-ray image pickup system 100 is equipped with a solid-state image pickup apparatus and an X-ray generator, and takes an image of an X-ray which is output from the X-ray generator to transmit through a subject A (i.e., a jaw portion of a test subject) by the solid-state image pickup apparatus.

The X-ray image pickup system 100 shown in this diagram is equipped with a solid-state image pickup apparatus 1A, an X-ray generator 106, and a rotation controlling section 108 supporting the solid-state image pickup apparatus 1A rotatably.

The X-ray generator 106 generates an X-ray toward the subject A. A radiation field of the X-ray generated from the X-ray generator 106 is controlled by a primary slit plate 106b. An X-ray tube is built into the X-ray generator 106, and the conditions such as a tube voltage, a tube current, and an energization time of the X-ray tube are adjusted, to control an X-ray irradiance level to the subject A. Further, the X-ray generator 106 is capable of outputting an X-ray at a predetermined spread angle in a certain imaging mode and outputting an X-ray at a spread angle narrower than the predetermined spread angle in the other imaging mode by controlling an opening range of the primary slit plate 106b.

The solid-state image pickup apparatus 1A is a CMOS-type solid-state image pickup apparatus having a plurality of pixels which are two-dimensionally arrayed, and converts an X-ray image passing through the subject A into electrical image data D. A secondary slit plate 107 restricting an X-ray incident area is provided on the front of the solid-state image pickup apparatus 1A. The rotation controlling section 108 supports the solid-state image pickup apparatus 1A rotatably around an axis line C vertical to a photosensitive surface 11 of the solid-state image pickup apparatus 1A, and rotates the solid-state image pickup apparatus 1A to a predetermined angular position corresponding to an imaging mode such as CT scan, panoramic radiography, or cephalometrical radiography.

The X-ray image pickup system 100 is further equipped with a swivel arm 104. The swivel arm 104 holds the X-ray generator 106 and the solid-state image pickup apparatus 1A such that those face each other, to swivel those around the subject A in CT scan, panoramic radiography, or cephalometrical radiography. Further, in linear tomography, a slide mechanism 113 for linearly displacing the solid-state image pickup apparatus 1A with respect to the subject A is provided. The swivel arm 104 is driven by an arm motor 109 composing a rotating table, and its rotation angle is detected by an angle sensor 112. Further, the arm motor 109 is mounted on a movable portion of an XY table 114, and its rotation center is arbitrarily adjusted in horizontal plane.

The image data D output from the solid-state image pickup apparatus 1A is once taken into a CPU (central processing unit) 121, and is stored in frame memories 122. A tomographic image or a panoramic image along an arbitrary tomographic plane is reproduced by predetermined arithmetic processing from the image data stored in the frame memories 122. The reproduced tomographic image or panoramic image is output to a video memory 124, and converted into an analog signal by a DA converter 125, and thereafter, the image is displayed by an image display 126 such as a CRT (cathode-ray tube), to be presented for various diagnoses.

A work memory 123 necessary for signal processing is connected to the CPU 121, and an operation panel 119 equipped with panel switches, an X-ray irradiation switch, and the like is further connected to the CPU 121. Further, the CPU 121 is connected respectively to a motor driving circuit 111 for driving the arm motor 109, slit control circuits 115 and 116 for controlling opening ranges of the primary slit plate 106b and the secondary slit plate 107, and an X-ray control circuit 118 for controlling the X-ray generator 106, and further, the CPU 121 outputs a clock signal for driving the solid-state image pickup apparatus 1A. The X-ray control circuit 118 feedback-controls an X-ray irradiance level to a subject on the basis of a signal taken as an image by the solid-state image pickup apparatus 1A.

Figure 2:
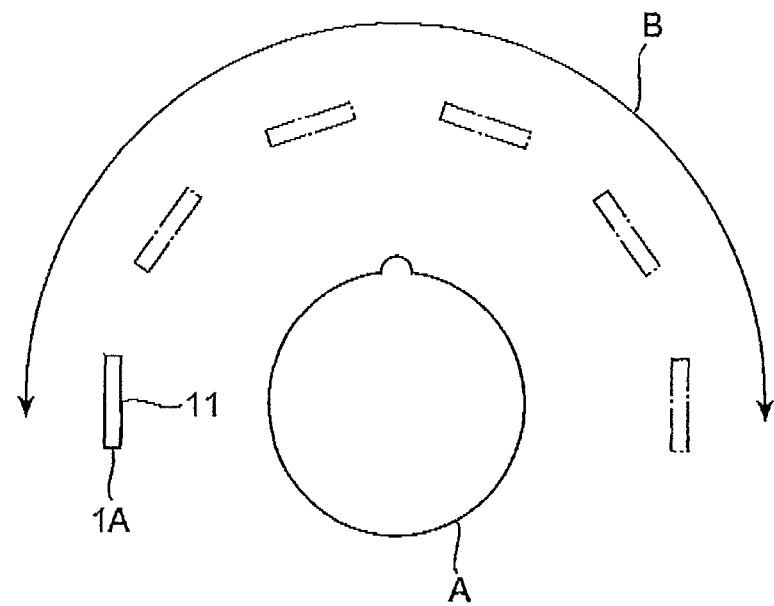
FIG. 2 is a diagram showing the situation that a solid-state image pickup apparatus 1A swivels around a subject A when viewed from above the subject A (a jaw portion of a test subject).

FIG. 2 is a diagram showing the situation that the solid-state image pickup apparatus 1A swivels around the subject A when viewed from above the subject A (a jaw portion of a test subject). In addition, in this drawing, the trajectory of the solid-state image pickup apparatus 1A is shown by a dashed line. The solid-state image pickup apparatus 1A takes an X-ray image passing through the subject A while moving circumferentially along the horizontal plane (arrow B in the drawing) centered on the subject A by the swivel arm 104. At this time, the orientation of the solid-state image pickup apparatus 1A is set such that the photosensitive surface 11 of the solid-state image pickup apparatus 1A always faces the subject A.

Figure 3:
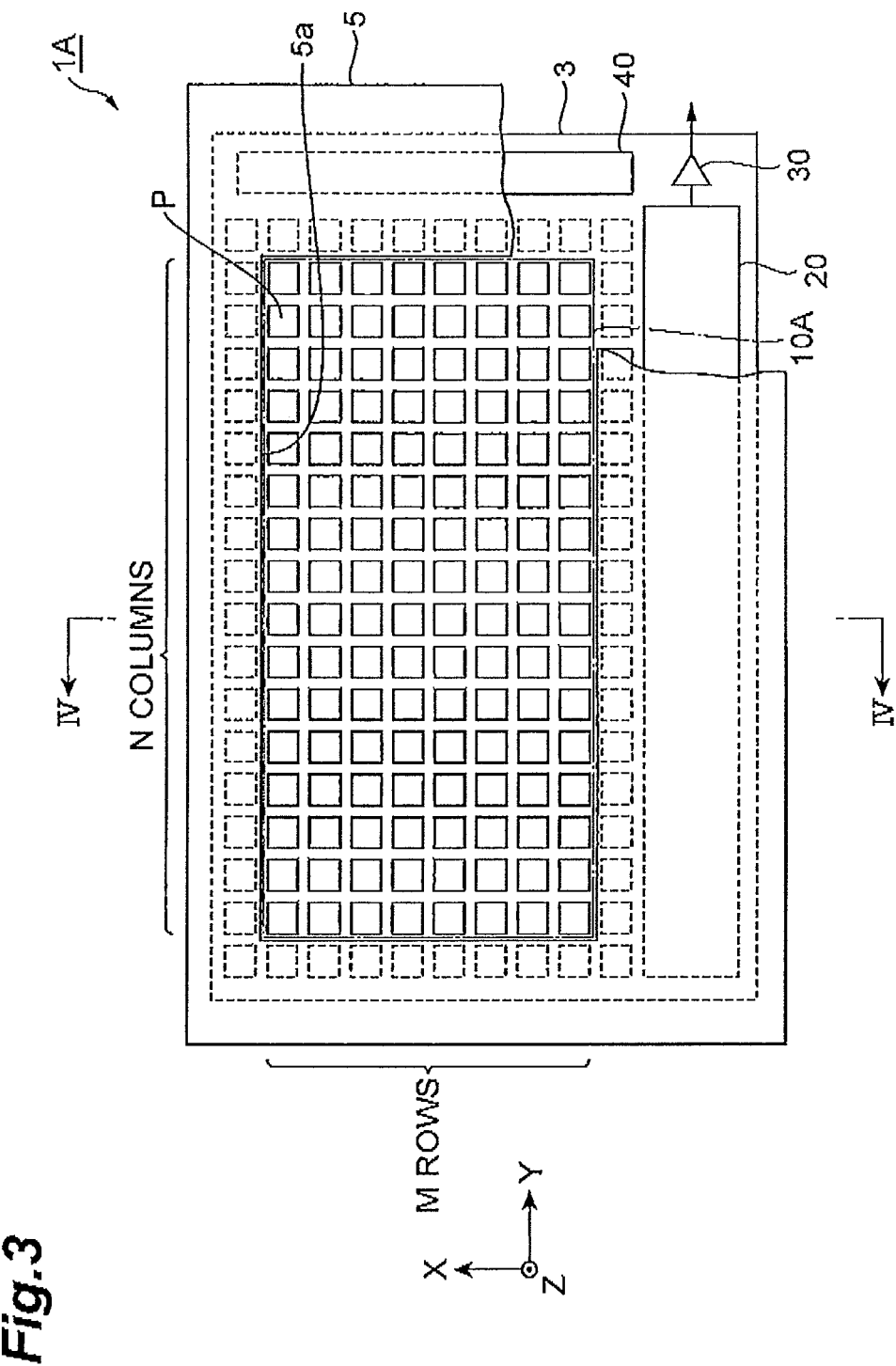
FIG. 3 is a plan view showing the solid-state image pickup apparatus 1A which is partially cut away.

FIGS. 3 and 4 are diagrams showing the configuration of the solid-state image pickup apparatus 1A in the present embodiment. FIG. 3 is a plan view showing the solid-state image pickup apparatus 1A which is partially cut away, and FIG. 4 is a sectional side view of the solid-state image pickup apparatus 1A along line IV-IV of FIG. 3. In addition, XYZ orthogonal coordinate systems are shown additionally in FIGS. 3 and 4 in order to facilitate understanding.

As shown in FIG. 3, the solid-state image pickup apparatus 1A is equipped with a photodetecting section 10A, a signal readout section 20, an A/D converting section 30, and a scanning shift register 40 which are created in the principal surface of a semiconductor substrate 3. In addition, the photodetecting section 10A, the signal readout section 20, the A/D converting section 30, and the scanning shift register 40 may be respectively formed on separate semiconductor substrates. Further, as shown in FIG. 4, the solid-state image pickup apparatus 1A is equipped with, in addition to the semiconductor substrate 3, a tabular base material 2, a scintillator 4, and an X-ray shielding section 5. The semiconductor substrate 3 is pasted on the base material 2, and the scintillator 4 is arranged on the semiconductor substrate 3. The scintillator 4 generates a scintillation light according to an incident X-ray, to convert the X-ray image into an optical image, and outputs this optical image to the photodetecting section 10A. The scintillator 4 is installed so as to cover the photodetecting section 10A, or provided on the photodetecting section 10A by vapor deposition. The X-ray shielding section 5 is composed of a material such as lead whose X-ray transmittance is extremely low. The X-ray shielding section 5 covers the marginal portion of the semiconductor substrate 3, and prevents the incidence of X-rays into the signal readout section 20 and the like.

The photodetecting section 10A is configured such that M×N pixels P are two-dimensionally arrayed in M rows and N columns. In addition, in FIG. 3, the column direction is matched to the X-axis direction and the row direction is matched to the Y-axis direction. Here, M and N are respectively greater than or equal to 2, and integers satisfying M<N. That is, the number of pixels P in the row direction in the photodetecting section 10A is greater than the number of pixels P in the column direction. Then, the photosensitive surface of the photodetecting section 10A forms a rectangle whose longitudinal direction is the row direction (Y-axis direction) and whose short-side direction is the column direction (X-axis direction). The respective pixels P are arrayed at a pitch of 100 μm, for example, and have a configuration in common with a PPS system.

In addition, on the semiconductor substrate 3, pixels are formed around the photodetecting section 10A as well. However, such pixels are covered with the X-ray shielding section 5, and light is not incident into those and charges are not generated, which does not contribute to taking an image. The photodetecting section 10A of the present embodiment includes the M×N pixels P two-dimensionally arrayed in M rows and N columns as pixels effective for taking an image. In other words, the area serving as the photodetecting section 10A on the semiconductor substrate 3 in the present embodiment is determined by an opening 5a of the X-ray shielding section 5.

The signal readout section 20 holds voltage values corresponding to the quantities of charges output from the respective pixels P of the photodetecting section 10A, and outputs the holding voltage values in series. The voltage values output from the signal readout section 20 are input to the A/D converting section 30, and the A/D converting section 30 performs analog-to-digital conversion processing with respect to the input voltage values (analog values), to output digital values corresponding to the input voltage values. The scanning shift register 40 controls the respective pixels P such that charges accumulated in the respective pixels P are output in series to the signal readout section 20 for each row.

The X-ray image pickup system 100 equipped with the solid-state image pickup apparatus 1A has imaging modes such as CT scan, panoramic radiography, and cephalometrical radiography as described above. Then, the solid-state image pickup apparatus 1A is supported rotatably around the axis line vertical to the photosensitive surface by the rotation controlling section 108, and controlled to a predetermined angular position according to an imaging mode. Further, the solid-state image pickup apparatus 1A has a function of changing an imaging area in the photodetecting section 10A (an area contributing to imaging data in the photodetecting section 10A) according to an imaging mode.

Figure 5:
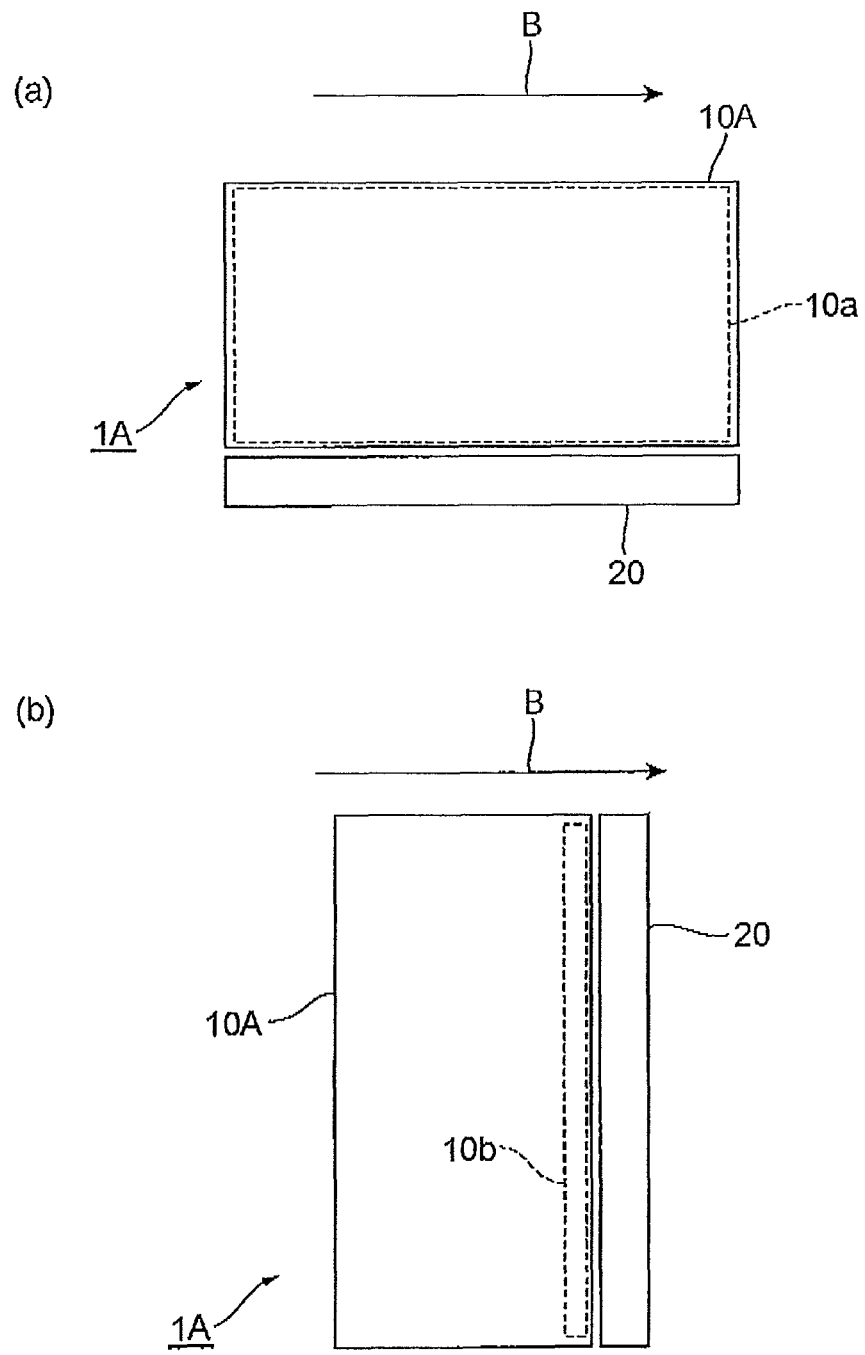
FIG. 5-($a$) is a diagram showing an angular position of the solid-state image pickup apparatus 1A according to an imaging mode, and an imaging area in a photodetecting section 10A, and a diagram showing the angular position of the solid-state image pickup apparatus 1A in an imaging mode such as CT scan (a first imaging mode) and an imaging area 10$a$ in the photodetecting section 10A.

Here, FIG. 5-(a) and FIG. 5-(b) are diagrams showing the angular positions of the solid-state image pickup apparatus 1A and the imaging areas in the photodetecting section 10A according to imaging modes. FIG. 5-(a) is a diagram showing the angular position of the solid-state image pickup apparatus 1A and an imaging area 10a in the photodetecting section 10A in an imaging mode such as CT scan (a first imaging mode). Further, FIG. 5-(b) is a diagram showing the angular position of the solid-state image pickup apparatus 1A and an imaging area 10b in the photodetecting section 10A in an imaging mode such as panoramic radiography or cephalometrical radiography (a second imaging mode). In addition, in FIG. 5-(a) and FIG. 5-(b), arrows B indicate the moving directions of the solid-state image pickup apparatus 1A by the swivel arm 104 (refer to FIG. 1).

As shown in FIG. 5-(a), in the first imaging mode such as CT scan, the rotation angle of the solid-state image pickup apparatus 1A is controlled such that the longitudinal direction (row direction) of the photodetecting section 10A is made along the moving direction B, more strictly, the row direction of the photodetecting section 10A is made parallel to the moving direction B. Further, the imaging area 10a at this time is composed of all the pixels P on M rows and N columns in the photodetecting section 10A. That is, the length in the row direction and the width in the column direction of the imaging area 10a are respectively the same as those of the photodetecting section 10A.

Further, as shown in FIG. 5-(b), in the second imaging mode such as panoramic radiography or cephalometrical radiography, the rotation angle of the solid-state image pickup apparatus 1A is controlled such that the longitudinal direction (row direction) of the photodetecting section 10A is made perpendicular to the moving direction B, in other words, made vertical to the swiveling plane of the photodetecting section 10A. Accordingly, for example, at the time of shifting from the CT scan mode to the panoramic radiography mode, the solid-state image pickup apparatus 1A is to rotate by 90 degrees. Further, the imaging area 10b at this time is composed of pixels P on successive $M_1$ rows among the pixels P arrayed in M rows (however, $M_1$<M). That is, the length in the row direction of the imaging area 10b is the same as that of the photodetecting section 10A, and the width in the column direction of the imaging area 10b is shorter than that of the photodetecting section 10A. Further, the imaging area 10b as described above is preferably arranged as close as possible to the signal readout section 20. For example, it is recommended that a range of $M_1$ rows counted in order from the row closest to the signal readout section 20 among the M rows in the photodetecting section 10A be served as the imaging area 10b. In addition, the imaging area 10b as described above is realized by selecting pixels P as targets from which charges are extracted by the scanning shift register 40 shown in FIG. 3.

In the X-ray image pickup system 100 according to the present embodiment, the following effect can be obtained by controlling the rotation angle of the solid-state image pickup apparatus 1A in this way. As described above, the photodetecting section 10A of the solid-state image pickup apparatus 1A has the rectangular photosensitive surface. Then, in the first imaging mode needing the imaging area 10a whose longitudinal direction is the moving direction B of the solid-state image pickup apparatus 1A and in the second imaging mode needing the imaging area 10b whose longitudinal direction is the direction perpendicular to the moving direction B of the solid-state image pickup apparatus 1A respectively, the longitudinal directions of the imaging areas 10a and 10b can be matched to the longitudinal direction of the photodetecting section 10A. Accordingly, in accordance with the X-ray image pickup system 100 according to the present embodiment, it is possible to realize the two imaging modes by the one solid-state image pickup apparatus 1A, and reduce the area of the photodetecting section 10A necessary for setting the imaging areas 10a and 10b of different shapes, which are necessary for the respective imaging modes in the one photodetecting section 10A.

Here, in the first imaging mode for carrying out CT scan, it is necessary to take a total width of a tooth row as an image by one-time radiography. Therefore, the size of the imaging area 10a is required to be, for example, 8 cm or more in height (that is, the width in the direction perpendicular to the moving direction B) and 12 cm or more in horizontal width (the width in the direction parallel to the moving direction B). Then, as shown in FIG. 6-(a), provided that the size of the imaging area 10a is, for example, 8 cm in height and 12 cm in horizontal width by performing square panelization onto the substantially circular silicon wafer W for the photodetecting section 10A, the size required for the first imaging mode is satisfied. However, in the second imaging mode for carrying out panoramic radiography, it is necessary to take an image of a jaw and its upper and lower tooth rows by one-time radiography. Therefore, the size of the imaging area 10b is required to be, for example, 15 cm or more in height (in addition, the horizontal width may be 7 mm or more). Accordingly, in the case where an attempt is made to realize both imaging modes by use of one solid-state image pickup apparatus, provided that these imaging areas are allotted without rotating the solid-state image pickup apparatus as in the configuration described in Patent Document 1, a photosensitive surface of 15 cm or more in height and 12 cm or more in horizontal width is necessary, which needs a greater silicon wafer.

In contrast thereto, as shown in FIG. 6-(b), for example, provided that the size of the photodetecting section 10A in the silicon wafer W is made into a rectangle of 15 cm×8 cm, it is possible to realize the photodetecting section 10A satisfying the size required for the imaging area 10b in the second imaging mode. Then, by rotating the photodetecting section 10A by 90 degrees as the solid-state image pickup apparatus 1A in the present embodiment, it is possible to satisfy the size required for the imaging area 10a in the first imaging mode as well. In this way, in accordance with the solid-state image pickup apparatus 1A according to the present embodiment, it is possible to set the imaging areas 10a and 10b of different shapes, which are necessary for the first imaging mode and the second imaging mode in the one photodetecting section 10A without increasing the area of the silicon wafer.

Further, for example, when the solid-state image pickup apparatus is used so as not to be rotated as in the configuration described in Patent Document 1, as shown in FIG. 7-(a) and FIG. 7-(b), the longitudinal direction of an imaging area 110a in the first imaging mode and the longitudinal direction of an imaging area 110b in the second imaging mode are perpendicular to one another in a photodetecting section 110. In such a configuration, as shown in FIG. 7-(a), for example, when a signal readout section 120 is arranged along the longitudinal direction of the imaging area 110a, although the number of pixels per column in the imaging area 110a is decreased (arrow $E_1$ in FIG. 7-(a)), the number of pixels per column in the imaging area 110b is increased (arrow $E_2$ in FIG. 7-(a)), which makes it take time to read out charges in the second imaging mode. Inversely, as shown in FIG. 7-(b), for example, when the signal readout section 120 is arranged along the longitudinal direction of the imaging area 110b, although the number of pixels per column in the imaging area 110b is decreased (arrow $E_3$ in FIG. 7-(b)), the number of pixels per column in the imaging area 110a is increased (arrow $E_4$ in FIG. 74)), which makes it take time to read out charges in the first imaging mode. In this way, when the respective imaging areas are allotted without rotating the solid-state image pickup apparatus, it takes time to read out charges in one of the first imaging mode and the second imaging mode, and a frame rate (the number of pieces of frame data to be output per unit time) is slowed.

Further, as shown in FIG. 8-(a) and FIG. 8-(b), even in the case where the shape of a photodetecting section 130 is made into a rectangle, and the solid-state image pickup apparatus is used so as to be rotated, when the number of columns N is less than the number of rows M (in other words, a signal readout section 140 is arranged along the short-side direction of the photodetecting section 130), the number of pixels per column is increased in both of an imaging area 130a in the first imaging mode and an imaging area 130b in the second imaging mode (arrow $E_3$ in FIG. 8-(a) and arrow $E_6$ in FIG. 8-(b)). In this case, it takes time to read out charges in both of the first imaging mode and the second imaging mode, which slows its frame rate.

In contrast to these cases, in the solid-state image pickup apparatus 1A according to the present embodiment, as shown in FIG. 9-(a) and FIG. 9-(b), the shape of the photosensitive surface of the photodetecting section 10A is a rectangle whose longitudinal direction is the row direction, where M<N, that is, the number of columns N of the pixels P is greater than the number of rows M. Then, as described above, the longitudinal directions of the imaging areas 10a and 10b in the respective imaging modes are matched to the longitudinal direction of the photodetecting section 10A. In the solid-state image pickup apparatus 1A, N readout wirings (which will be described later) for reading out charges from the respective pixels P are installed on the respective columns, and in accordance with the configuration thereof, the installing direction of the readout wirings and the short-side directions of the imaging areas 10a and 10b are always matched to one another in the respective imaging modes. Accordingly, since it is possible to decrease the number of pixels P as targets from which charges are readout through the readout wirings in the respective frames in any one of the imaging modes (arrow $E_7$ in FIG. 9-(a), arrow $E_8$ in FIG. 9-(b)), it is possible to shorten the time to read out charges, and further speed up its frame rate.

Further, as described above, the solid-state image pickup apparatus 1A is supported by the rotation controlling section 108, and controlled to an angular position according to an imaging mode. Here, FIG. 10-(a) and FIG. 10-(b) are diagrams showing the situations of rotation of the photodetecting section 10A according to the positions of the rotation center (the axis line C shown in FIG. 1) of the solid-state image pickup apparatus 1A. FIG. 10-(a) shows the case where the center E of the photodetecting section 10A is set as a rotation center of the solid-state image pickup apparatus 1A. Further, FIG. 10-(b) shows the case where one corner F among the four corners of the rectangular photodetecting section 10A is set as a rotation center of the solid-state image pickup apparatus 1A, and the solid-state image pickup apparatus 1A is rotated such that the corner F is located below the other corners throughout the first imaging mode and the second imaging mode (that is, the corner F is always located on the lower jaw side of the test subject). In addition, in FIG. 10-(a) and FIG. 10-(b), the diagrams shown by the solid line show the angular positions of the photodetecting section 10A in the second imaging mode such as panoramic radiography or cephalometrical radiography, and the diagrams shown by the dashed line show the angular positions of the photodetecting section 10A in the first imaging mode such as CT scan.

The rotation center of the solid-state image pickup apparatus 1A in the present embodiment may be set to various positions, for example, the center E in FIG. 10-(a) or the corner F in FIG. 10-(b). However, it is most preferable that the rotation center of the solid-state image pickup apparatus 1A is set to the corner F in FIG. 10-(b). When the solid-state image pickup apparatus 1A takes an X-ray image while moving around a jaw portion of a test subject, the lower jaw portion of the test subject is placed on a support table to fix the head position of the test subject in many cases, and in such a case, the standard for the position in height of the jaw portion of the test subject is to be the lower end of the jaw. Then, provided that the rotation center of the solid-state image pickup apparatus 1A is set to the corner F in FIG. 10-(b), the heights of the lower ends of the photo detecting section 10A in the first imaging mode and the second imaging mode can be matched to one another at the height of the corner F. Accordingly, it is possible to accurately match the height of the photodetecting section 10A and the height of the jaw portion of the test subject in both of the first imaging mode and the second imaging mode.

Figure 11:
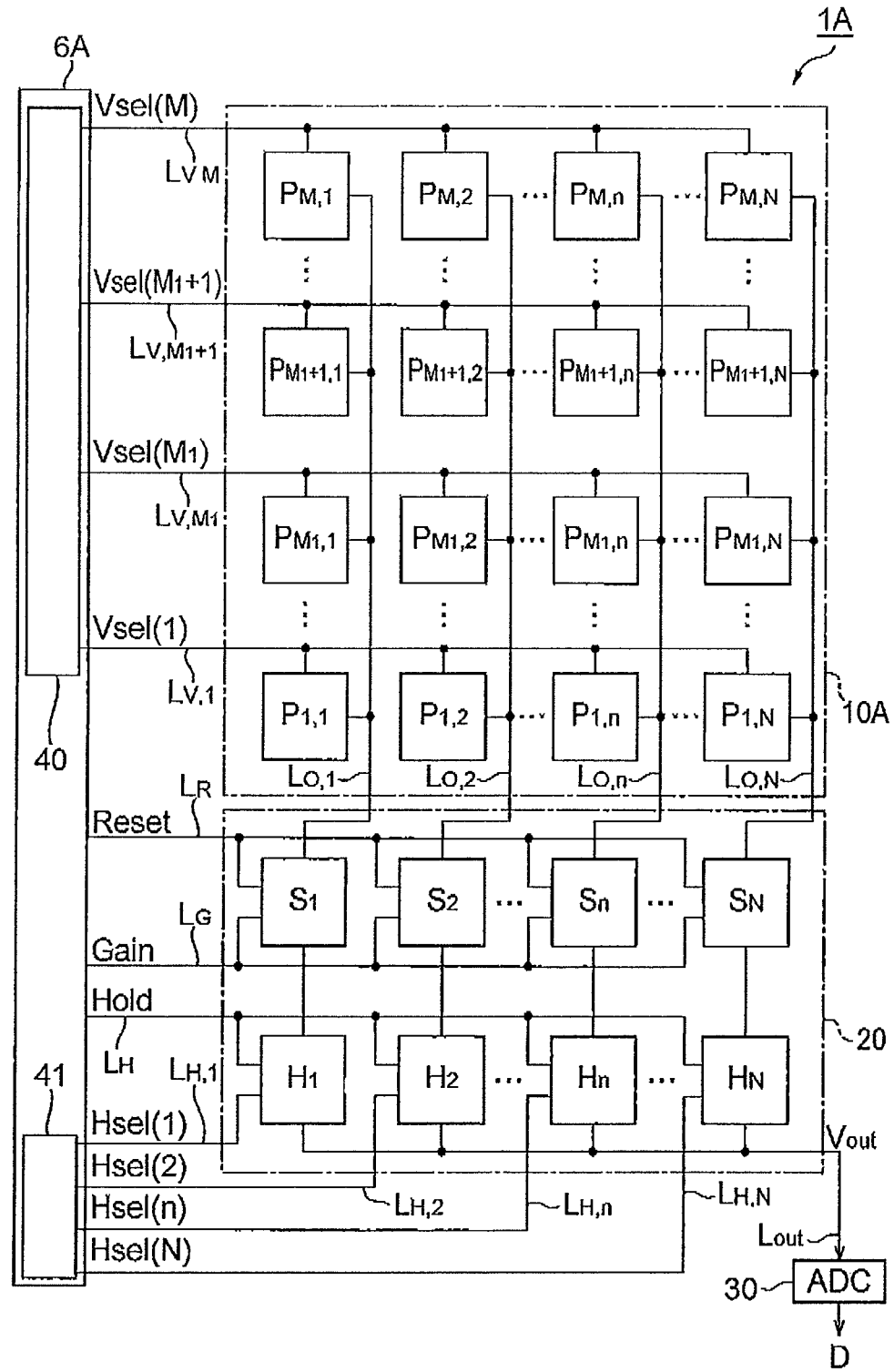
FIG. 11 is a diagram showing the internal configuration of the solid-state image pickup apparatus 1A according to the first embodiment.

Next, a detailed configuration of the solid-state image pickup apparatus 1A according to the present embodiment will be described. FIG. 11 is a diagram showing the internal configuration of the solid-state image pickup apparatus 1A. The photodetecting section 10A is formed such that M×N pixels $P_{1,1}$ to $P_{M,N}$ are two-dimensionally arrayed in M rows and N columns. A pixel $P_{m,n}$ is located on the m-th row and the n-th column. Where m is a respective integer which is one or more and M or less, and n is a respective integer which is one or more and N or less. N pixels $P_{m,1}$ to $P_{m,N}$ on the m-th row are respectively connected to the scanning shift register 40 through the m-th row selecting wirings $L_{V,m}$. In addition, in FIG. 11, the scanning shift register 40 is included in a controlling section 6A. The respective output terminals of M pixels $P_{1,n}$ to $P_{M,n}$ on the n-th column are connected to an integrating circuit $S_n$ of the signal readout section 20 through the n-th column readout wirings $L_{O,n}$.

The signal readout section 20 includes N integrating circuits $S_1$ to $S_N$ and N holding circuits $H_1$ to $H_N$. The respective integrating circuits $S_n$ have a common configuration. Further, the respective holding circuits $H_n$ have a common configuration. The respective integrating circuits $S_n$ have input terminals connected to the readout wirings $L_{O,n}$, and accumulate charges input to the input terminals and output voltage values corresponding to the quantities of the accumulated charges to the holding circuits $H_n$ from their output terminals. The N integrating circuits $S_1$ to $S_N$ are respectively connected to the controlling section 6A through a resetting wiring $L_R$, and connected to the controlling section 6A through a gain setting wiring $L_G$. Each holding circuit $H_n$ has an input terminal connected to the output terminal of the integrating circuit $S_n$, and holds a voltage value input to the input terminal, and outputs the holding voltage value to a voltage outputting wiring $L_{out}$ from its output terminal. The N holding circuits $H_1$ to $H_N$ are respectively connected to the controlling section 6A through a holding wiring $L_H$, and connected to a readout shift register 41 of the controlling section 6A through n-th, column selecting wirings $L_{H,n}$.

Voltage values output from the N holding circuits $H_1$ to $H_N$ to the voltage outputting wiring $L_{out}$ are input to the A/D converting section 30, and the A/D converting section 30 performs analog-to-digital conversion processing with respect to the input voltage values (analog values), to output digital values corresponding to the input voltage values as image data D.

The scanning shift register 40 in the controlling section 6A outputs an m-th row selection control signal Vsel (m) to an m-th row selecting wiring $L_{V,m}$, and provides the m-th row selection control signal Vsel (m) to the N respective pixels $P_{m,1}$ to $P_{m,N}$ on the m-th row. M row selection control signals Vsel (1) to Vsel (M) are made into significant values in series. Further, the readout shift register 41 of the controlling section 6A outputs an n-th column selection control signal Hsel (n) to an n-th selecting wiring $L_{H,n}$, and provides the n-th column selection control signal Hsel (n) to the holding circuit $H_n$. The n-th column selection control signals Hsel (1) to Hsel (N) as well are made into significant values in series.

Further, the controlling section 6A outputs a reset control signal Reset to the resetting wiring $L_R$, and provides the reset control signal Reset respectively to the N integrating circuits $S_1$ to $S_N$. The controlling section 6A outputs a gain setting signal Gain to the gain setting wiring $L_G$, and provides the gain setting signal Gain respectively to the N integrating circuits $S_1$ to $S_N$. The controlling section 6A outputs a holding control signal Hold to the holding wiring $L_H$, and provides the holding control signal Hold respectively to the N holding circuits $H_1$ to $H_N$. Moreover, although not shown in the drawings, the controlling section 6A controls analog-to-digital conversion processing in the A/D converting section 30 as well.

Figure 12:
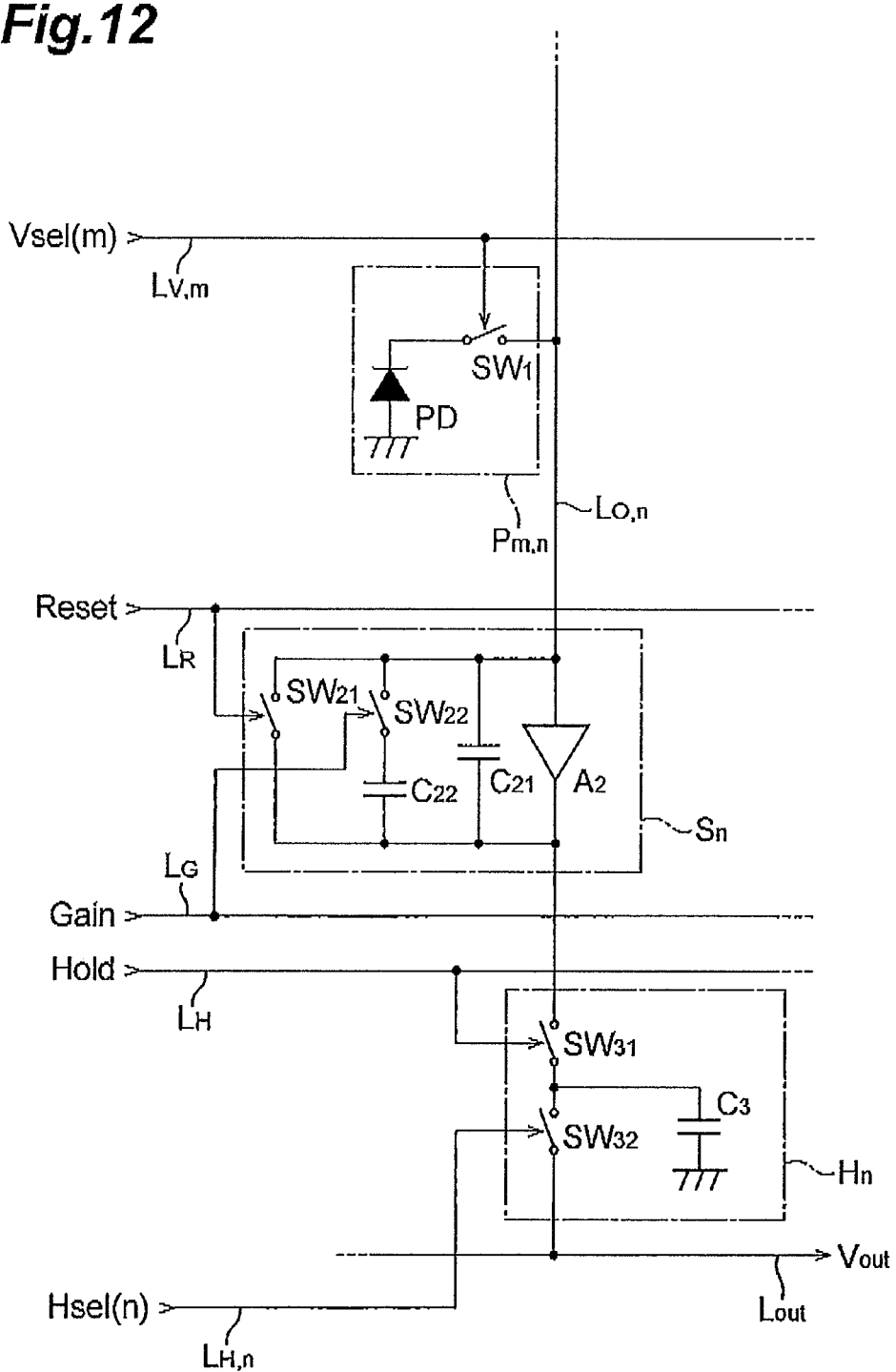
FIG. 12 shows respective circuit diagrams of a pixel $P_{m,n}$, an integrating circuit $S_n$, and a holding circuit $H_n$ of the solid-state image pickup apparatus 1A according to the first embodiment.

FIG. 12 shows respective circuit diagrams of the pixel $P_{m,n}$, the integrating circuit $S_n$, and the holding circuit $H_n$ in the solid-state image pickup apparatus 1A. Here, the circuit diagram of the pixel $P_{m,n}$ is shown as a representative of the M×N pixels $P_{1,1}$ to $P_{M,N}$, the circuit diagram of the integrating circuit $S_n$ is shown as a representative of the N integrating circuits $S_1$ to $S_N$, and the circuit diagram of the holding circuit $H_n$ is shown as a representative of the N holding circuits $H_1$ to $H_N$. That is, the circuit portion associated with the pixel $P_{m,n}$ on the m-th row and the n-th column and the n-th column readout wiring $L_{O,n}$ is shown.

The pixel $P_{m,n}$ includes a photodiode PD and a readout switch $SW_1$. The anode terminal of the photodiode PD is grounded, and the cathode terminal of the photodiode PD is connected to the n-th column readout wiring $L_{O,n}$ via the readout switch $SW_1$. The photodiode PD generates charges of an amount corresponding to an incident light intensity, and accumulates the generated charges in a junction capacitance section of the photodiode PD itself. The readout switch $SW_1$ is provided with the m-th row selection control signal Vsel (m) passing through the m-th row selecting wiring $L_{V,m}$ from the controlling section 6A. The m-th row selection control signal Vsel (m) is for instructing a switching operation of the readout switch $SW_1$ of each of the N pixels $P_{m,1}$ to $P_{m,N}$ on the m-th row in the photodetecting section 10A.

In this pixel $P_{m,n}$, when the m-th row selection control signal Vsel (m) is at a low level, the readout switch $SW_1$ is opened, and the charges generated in the photodiode PD are not output to the n-th column readout wiring $L_{O,n}$, but accumulated in the junction capacitance section of the photodiode PD itself. On the other hand, when the m-th row selection control signal Vsel (m) is at a high level, the readout switch $SW_1$ is closed, and the charges generated in the photodiode PD to be accumulated in the junction capacitance section of the photodiode PD itself until that moment are output to the n-th column readout wiring $L_{O,n}$ via the readout switch $SW_1$.

The n-th column readout wiring $L_{O,n}$ is connected to the respective readout switches $SW_1$ of the M pixels $P_{1,n}$ to $P_{M,n}$ on the n-th column in the photodetecting section 10A. The n-th column readout wiring $L_{O,n}$ reads out charges generated in the photodiode PD of one pixel of the M pixels $P_{1,n}$ to $P_{M,n}$, via the readout switch $SW_1$ of the pixel, to transfer those to the integrating circuit $S_n$.

The integrating circuit $S_n$ includes an amplifier $A_2$, an integral capacitor $C_{21}$, an integral capacitor $C_{22}$, a discharging switch $SW_{21}$, and a gain setting switch $SW_{22}$. The integral capacitor $C_{21}$ and the discharging switch $SW_{21}$ are connected in parallel with each other, and provided between the input terminal and the output terminal of the amplifier $A_2$. Further, the integral capacitor $C_{22}$ and the gain setting switch $SW_{22}$ are connected in series with each other, and provided between the input terminal and the output terminal of the amplifier $A_2$ such that the gain setting switch $SW_{22}$ is connected to the input terminal side of the amplifier $A_2$. The input terminal of the amplifier $A_2$ is connected to the n-th column readout wiring $L_{O,n}$.

The reset control signal Reset passing through the resetting wiring $L_R$ from the controlling section 6A is provided to the discharging switch $SW_{21}$. The reset control signal Reset is for instructing a switching operation of the discharging switch $SW_{21}$ of each of the N integrating circuits $S_1$ to $S_N$. A gain setting signal Gain passing through the gain setting wiring $L_G$ from the controlling section 6A is provided to the gain setting switch $SW_{22}$. The gain setting signal Gain is for instructing a switching operation of the gain setting switch $SW_{22}$ of each of the N integrating circuits $S_1$ to $S_N$.

In this integrating circuit $S_n$, the integral capacitors $C_{21}$ and $C_{22}$ and the gain setting switch $SW_{22}$ compose a feedback capacitance section whose capacitance value is variable. That is, when a gain setting signal Gain is at a low level and the gain setting switch $SW_{22}$ is opened, the capacitance value of the feedback capacitance section is equal to the capacitance value of the integral capacitor $C_{21}$. On the other hand, when a gain setting signal Gain is at a high level and the gain setting switch $SW_{22}$ is closed, the capacitance value of the feedback capacitance section is equal to a sum of the respective capacitance values of the integral capacitors $C_{21}$ and $C_{22}$. When a reset control signal Reset is at a high level, the discharging switch $SW_{21}$ is closed, the feedback capacitance section is discharged, and a voltage value output from the integrating circuit $S_n$ is initialized. On the other hand, when a reset control signal Reset is at a low level, the discharging switch $SW_{21}$ is opened, charges input to the input terminal are accumulated in the feedback capacitance section, and a voltage value corresponding to an amount of the accumulated charges is output from the integrating circuit $S_n$.

The holding circuit $H_n$ includes an inputting switch $SW_{31}$, an outputting switch $SW_{32}$, and a holding capacitor $C_3$. One end of the holding capacitor $C_3$ is grounded. The other end of the holding capacitor $C_3$ is connected to the output terminal of the integrating circuit $S_n$ via the inputting switch $SW_{31}$, and connected to the voltage outputting wiring $L_{out}$ via the outputting switch. $SW_{32}$. The holding control signal Hold passing through the holding wiring $L_H$ from the controlling section 6A is provided to the inputting switch $SW_{31}$. The holding control signal Hold is for instructing a switching operation of the inputting switch $SW_{31}$ of each of the N holding circuits $H_1$ to $H_N$. An n-th column selection control signal Hsel (n) passing through the n-th column selecting wiring $L_{H,n}$ from the controlling section 6A is provided to the outputting switch $SW_{32}$. The n-th column selection control signal Hsel (n) is for instructing a switching operation of the outputting switch $SW_{32}$ of each holding circuit $H_n$.

In this holding circuit $H_n$, when the holding control signal Hold is shifted from the high level to a low level, the inputting switch $SW_{31}$ is shifted from a closed state to an open state, and a voltage value input to the input terminal at that time is held in the holding capacitor $C_3$. Further, when an n-th column selection control signal Hsel (n) is at a high level, the outputting switch $SW_{32}$ is closed, and a voltage value held in the holding capacitor $C_3$ is output to the voltage outputting wiring $L_{out}$.

At the time of outputting voltage values corresponding to the respective received light intensities of the N pixels $P_{m,1}$ to $P_{m,N}$ on the m-th row in the photodetecting section 10A, the controlling section 6A instructs to once close and then open the respective discharging switches $SW_{21}$ of the N integrating circuits $S_1$ to $S_N$ by use of the reset control signal Reset, and thereafter, instructs to close the respective readout switches $SW_1$ of the N pixels $P_{m,1}$ to $P_{m,N}$ on the m-th row in the photo detecting section 10A over a predetermined period by use of the m-th row selection control signal Vsel (m). The controlling section 6A instructs to shift the respective inputting switches $SW_{31}$ of the N holding circuits $H_1$ to $H_N$ from a closed state to an open state by use of the holding control signal Hold during the predetermined period. Then, the controlling section 6A instructs to close the respective outputting switches $SW_{32}$ of the N holding circuits $H_1$ to $H_N$ in series only during a given period by use of the column selection control signals Hsel (1) to Hsel (N) after the predetermined period. The controlling section 6A performs controls as described above in series for the respective rows.

In this way, the controlling section 6A controls a switching operation of the readout switches $SW_1$ of each of the M×N pixels $P_{1,1}$ to $P_{M,N}$ in the photodetecting section 10A, and controls a holding operation and an outputting operation for a voltage value in the signal readout section 20. Thereby, the controlling section 6A repeatedly outputs voltage values corresponding to the quantities of charges generated in the respective photodiodes PD of the M×N pixels $P_{1,1}$ to $P_{M,N}$ in the photodetecting section 10A as frame data from the signal readout section 20.

As described above, the solid-state image pickup apparatus 1A according to the present embodiment has the first imaging mode such as CT scan and the second imaging mode such as panoramic radiography or cephalometrical radiography. Then, as shown in FIG. 5, the imaging areas in the photodetecting section 10A in the first imaging mode and the second imaging mode are different from each other (the area 10a in FIG. 5-(a) in the first imaging mode and the area 10b in FIG. 5-(b) in the second imaging mode). Then, the controlling section 6A outputs voltage values corresponding to the quantities of charges generated in the respective photodiodes PD of the M×N pixels $P_{1,1}$ to $P_{M,N}$ in the photodetecting section 10A from the signal readout section 20 in the first imaging mode. Further, the controlling section 6A outputs voltage values corresponding to the quantities of charges generated in the photodiodes PD of the respective pixels $P_{m,n}$ included in a specific range of the successive $M_1$ rows ($M_1$; an integer less than, M) in the photodetecting section 10A from the signal readout section 20 in the second imaging mode.

In this second imaging mode, it is preferable that the imaging area 10b is arranged so as to be close to the signal readout section 20. Accordingly, the controlling section 6A preferably sets a range of the $M_1$ rows counted in order from the row closest to the signal readout section 20 among the M rows in the photodetecting section 10A as the above-described specific range. That is, as shown in FIG. 9, in the case where the row closest to the signal readout section 20 in the photodetecting section 10A is the first row, it is preferable that, in the second imaging mode, the controlling section 6A sets a range from the first row to the $M_1$-th row in the photodetecting section 10A as the above-described specific range, and outputs voltage values corresponding to the quantities of charges generated in the photodiodes PD of the respective pixels $P_{m,n}$ in this specific range (from the first row to the $M_1$-th row) from the signal readout section 20.

Here, FIG. 13-(a) and FIG. 13-(b) are diagrams for explanation of advantages of arranging the imaging area 10b in the second imaging mode so as to be close to the signal readout section 20. Here, the case where a fault such as disconnection is caused in the n-th column readout wiring $L_{O,n}$ is considered. For example, as shown in FIG. 13-(a), in the case where the imaging area 10b is arranged near the center of the photodetecting section 10A, when a disconnection DL of the n-th column readout wiring $L_{O,n}$ is caused between the signal readout section 20 and the imaging area 10b, it is impossible to transmit charges from pixels farther away from the disconnection DL when viewed from the signal readout section 20 among the pixels arranged on the column, which causes a loss (so-called defect) in the image. Then, since the moving direction B of the solid-state image pickup apparatus 1A and the column direction of the photodetecting section 10A are parallel to one another in the second imaging mode, such a loss in an image remains in a panoramic image or the like obtained by successively taking images while moving the solid-state image pickup apparatus 1A.

In contrast thereto, as shown in FIG. 13-(b), in the case where the imaging area 10b is arranged so as to be close to the signal readout section 20, even when a disconnection DL of the n-th column readout wiring $L_{O,n}$ is caused, the probability that the caused position exists between the signal readout section 20 and the imaging area 10b is low. Accordingly, the probability of being incapable of reading out charges from pixels arranged on the column in the imaging area 10b can be lowered, which enables to prevent a defect from being caused.

Further, in the second imaging mode, the controlling section 6A reduces a readout pixel pitch in frame data based on a voltage value output from the signal readout section 20 as compared to the first imaging mode, speeds up a frame rate, that is the number of pieces of frame data to be output per unit time, and increases gain, that is a ratio of an output voltage value to an amount of input charges in the signal readout section 20. For example, in the first imaging mode such as CT scan, a pixel pitch is 200 μm, and a frame rate (the number of frames (F) per second (s)) is 30 F/s. Further, in the second imaging mode such as panoramic radiography or cephalometrical radiography, a pixel pitch is 100 μm, and a frame rate is 300 F/s.

In this way, as compared to the first imaging mode, its pixel pitch is less and its frame rate is higher in the second imaging mode. Accordingly, in the first imaging mode, it is necessary to perform binning-readout in order to set a pixel pitch greater than that in the second imaging mode. Further, as compared to the first imaging mode, its frame rate is higher in the second imaging mode, and therefore, an amount of light which the respective pixels of the respective frame data receive is less.

Then, the controlling section 6A makes a gain that is a ratio of an output voltage value to an amount of input charges in the signal readout section 20 differ in the first imaging mode and in the second imaging mode. That is, in the case where each integrating circuits $S_n$ is configured as shown in FIG. 12, the controlling section 6A controls the switching of the gain setting switch $SW_{22}$ by use of the gain setting signal Gain, to appropriately set a capacitance value of the feedback capacitance section of each integrating circuit to make a gain differ in the first imaging mode and in the second imaging mode.

In more detail, in the first imaging mode, a capacitance value of the feedback capacitance section is made equal to a sum of the respective capacitance values of the integral capacitor $C_{21}$ and the integral capacitor $C_{22}$ by closing the gain setting switch $SW_{22}$. On the other hand, in the second imaging mode, a capacitance value of the feedback capacitance section is made equal to a capacitance value of the integral capacitor $C_{21}$ by opening the gain setting switch $SW_{22}$. In this way, as compared to the first imaging mode, a capacitance value of the feedback capacitance section of each integrating circuit $S_n$ is made less, to increase a gain in the second imaging mode. Thereby, pixel data for a certain quantity of light can be made to be values close to each other in the first imaging mode and the second imaging mode, which enables to perform preferred operations in the respective imaging modes.

Next, the operation of the solid-state image pickup apparatus 1A according to the first embodiment will be described in detail. In the solid-state image pickup apparatus 1A according to the present embodiment, under the control by the controlling section 6A, the M row selection control signals Vsel (1) to Vsel (M), the N column selection control signals Hsel (1) to Hsel (N), the reset control signal Reset, and the holding control signal Hold are respectively changed in level at given timings, which enables to take an image of light made incident into the photodetecting section 10A to obtain frame data.

Figure 14:
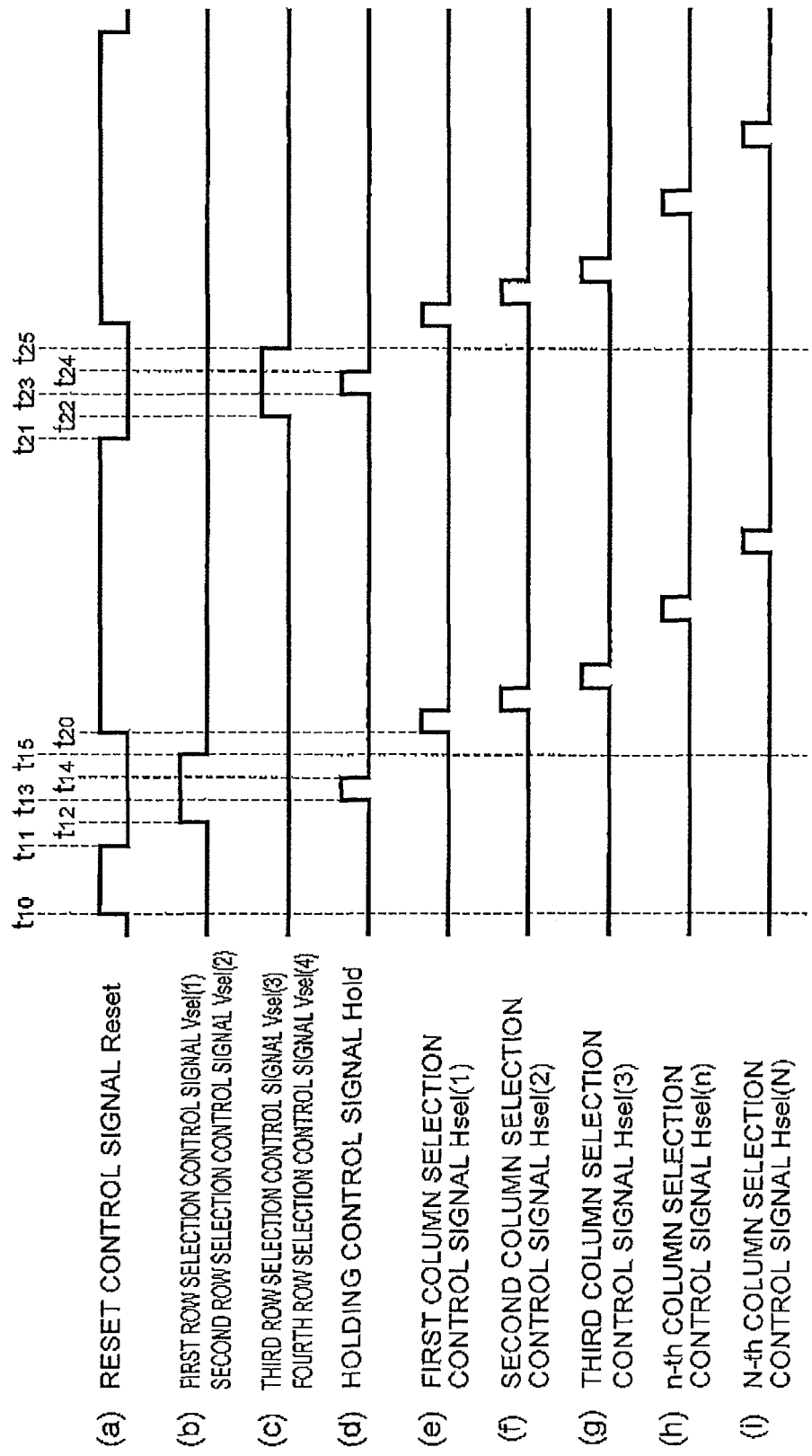
FIG. 14 is a timing chart for explanation of the operation of the solid-state image pickup apparatus 1A according to the first embodiment.

The operation of the solid-state image pickup apparatus 1A in the first imaging mode is as follows. FIG. 14 is a timing chart for explanation of the operation of the solid-state image pickup apparatus 1A according to the first embodiment. Here, the operation in the first imaging mode for performing binning-readout of two rows and two columns will be described. That is, a readout pixel pitch in frame data is set twice as much as a pixel pitch. In each integrating circuit $S_n$, the gain setting switch $SW_{22}$ is closed, a capacitance value of the feedback capacitance section is set to a higher value and a gain is set to a lower value.

In this drawing, (a) the reset control signal Reset for instructing switching operations of the respective discharging switches $SW_{21}$ of the N integrating circuits $S_1$ to $S_N$, (b) the first row selection control signal Vsel (1) and the second row selection control signal Vsel (2) for instructing switching operations of the respective readout switches $SW_1$ of the pixels $P_{1,1}$ to $P_{1,N}$ and $P_{2,1}$ to $P_{2,N}$ on the first row and the second row in the photodetecting section 1A, (c) the third row selection control signal Vsel (3) and the fourth row selection control signal Vsel (4) for instructing switching operations of the respective readout switches $SW_1$ of the pixels $P_{3,1}$ to $P_{3,N}$ and $P_{4,1}$ to $P_{4,N}$ on the third row and fourth, row in the photodetecting section 1A, and (d) the holding control signal Hold for instructing switching operations of the respective inputting switches $SW_{31}$ of the N holding circuits $H_1$ to $H_N$ are shown in order from the top.

Also, in this drawing, further in order continuously, (e) the first column selection control signal Hsel (1) for instructing a switching operation of the outputting switch $SW_{32}$ of the holding circuit $H_1$, (f) the second column selection control signal Hsel (2) for instructing a switching operation of the outputting switch $SW_{32}$ of the holding circuit $H_2$, (g) the third column selection control signal Hsel (3) for instructing a switching operation of the outputting switch $SW_{32}$ of the holding circuit $H_3$, (h) the n-th column selection control signal Hsel (n) for instructing a switching operation of the outputting switch $SW_{32}$ of the holding circuit $H_n$, and (i) the N-th column selection control signal Hsel (N) for instructing a switching operation of the outputting switch $SW_{32}$ of the holding circuit $H_N$ are shown.

The readout of the charges generated in the respective photodiodes PD of 2N pixels $P_{1,1}$ to $P_{1,N}$ and $P_{2,1}$ to $P_{2,N}$ on the first row and the second row, and accumulated in the junction capacitance sections thereof is performed as follows. Before time $t_{10}$, the M row selection control signals Vsel (1) to Vsel (M), the N column selection control signals Hsel (1) to Hsel (N), the reset control signal Reset, and the holding control signal Hold are respectively set to a low level.

During the period from time $t_{10}$ to time $t_{11}$, the reset control signal Reset output from the controlling section 6A to the resetting wiring $L_R$ is raised to a high level, thereby closing the discharging switches $SW_{21}$ and the integral capacitors $C_{21}$ and $C_{22}$ are discharged in the N respective integrating circuits $S_1$ to $S_N$. Further, during the period from time $t_{12}$ to time $t_{15}$ after time $t_{11}$, the first row selection control signal Vsel (1) output from the controlling section 6A to the first row selecting wiring $L_{V,1}$ is raised to a high level, thereby closing the respective readout switches $SW_1$ of the N pixels $P_{1,1}$ to $P_{1,N}$ on the first row in the photodetecting section 10A. Further, during this same period (from time $t_{12}$ to time $t_{15}$), the second row selection control signal Vsel (2) output from the controlling section 6A to the second row selecting wiring $L_{V,2}$ is raised to a high level, thereby closing the respective readout switches $SW_1$ of the N pixels $P_{2,1}$ to $P_{2,N}$ on the second row in the photodetecting section 10A.

During the period from time $t_{13}$ to time $t_{14}$ in this period (from time $t_{12}$ to time $t_{15}$), the holding control signal Hold output from the controlling section 6A to the holding wiring $L_H$ is raised to a high level, thereby closing the inputting switches $SW_{31}$ in the N respective holding circuits $H_1$ to $H_N$.

During the period (from time $t_{12}$ to time $t_{15}$), the readout switches $SW_1$ of the respective pixels $P_{1,n}$ and $P_{2,n}$ on the first row and the second row are closed, and the discharging switches $SW_{21}$ of the respective integrating circuits $S_n$ are open. Accordingly, the charges generated in the photodiode PD of the pixel $P_{1,n}$ and accumulated in the junction capacitance section of the photodiode PD itself until that moment are transferred to the integral capacitors $C_{21}$ and $C_{22}$ of the integrating circuit $S_n$ via the readout switch $SW_1$ of the pixel $P_{1,n}$ and the n-th column readout wiring $L_{O,n}$, to be accumulated. Further, at the same time, the charges generated in the photodiode PD of the pixel $P_{2,n}$ and accumulated in the junction capacitance section of the photodiode PD itself until that moment as well are transferred to the integral capacitors $C_{21}$ and $C_{22}$ of the integrating circuit $S_n$ via the readout switch $SW_1$ of the pixel $P_{2,n}$ and the n-th column readout wiring $L_{O,n}$, to be accumulated. Then, voltage values according to the quantities of charges accumulated in the integral capacitors $C_{21}$ and $C_{22}$ of the respective integrating circuits $S_n$ are output from the output terminals of the integrating circuits $S_n$.

When the holding control signal Hold is shifted from a high level to a low level at time $t_{14}$ of that period (from time $t_{12}$ to time $t_{15}$), the inputting switches $SW_{31}$ are shifted from a closed state to an open state in the N respective holding circuits $H_1$ to $H_N$, and the voltage values output from the output terminals of the integrating circuits $S_n$ at that time to be input to the input terminals of the holding circuits $H_n$ are held in the holding capacitors C3.

Then, after the period (from time $t_{12}$ to time $t_{15}$), the column selection control signals Hsel (1) to Hsel (N) output from the controlling section 6A to the column selecting wirings $L_{H,1}$ to $L_{H,N}$ are raised to a high level in series only during a given period, thereby closing the respective outputting switches $SW_{32}$ of the N holding circuits $H_1$ to $H_N$ in series only during the given period, and the voltage values held in the holding capacitors $C_3$ of the respective holding circuits $H_n$ are output in series to the voltage outputting wiring $L_{out}$ via the outputting switches $SW_{32}$. The voltage values $V_{out}$ output to the voltage outputting wiring $L_{out}$ indicate values that the received light intensities in the respective photodiodes PD of the 2N pixels $P_{1,1}$ to $P_{1,N}$ and $P_{2,1}$ to $P_{2,N}$ on the first row and the second row are added in the column direction.

The voltage values output in series from the N respective holding circuits $H_1$ to $H_N$ are input to the A/D converting section 30, and converted into digital values corresponding to the input voltage values. Then, among the N digital values output from the A/D converting section 30, digital values respectively corresponding to the first row and the second row are added, digital values respectively corresponding to the third row and the fourth row are added, and digital values are added two by two thereafter.

The readout of the charges generated in the respective photodiodes PD of the 2N pixels $P_{3,1}$ to $P_{3,N}$ and $P_{4,1}$ to $P_{4,N}$ on the third row and the fourth row, and accumulated in the junction capacitance sections of the photodiodes PD themselves is performed as follows.

During the period from time $t_{20}$ at which the column selection control signal Hsel (1) is raised to a high level to time $t_{21}$ after the time at which the column selection control signal Hsel (N) is once raised to a high level to be lowered to a low level in the aforementioned operation, the reset control signal Reset output from the controlling section 6A to the resetting wiring $L_R$ is raised to a high level, thereby closing the discharging switches $SW_{21}$, and the integral capacitors $C_{21}$ and $C_{22}$ are discharged in the N respective integrating circuits $S_1$ to $S_N$. Further, during the period from time $t_{22}$ to time $t_{25}$ after time $t_{21}$, the third row selection control signal Vsel (3) output from the controlling section 6A to the third row selecting wiring $L_{V,3}$ is raised to a high level, thereby closing the respective readout switches $SW_1$ of the N pixels $P_{3,1}$ to $P_{3,N}$ on the third row in the photodetecting section 10A. Further, during this same period (from time $t_{22}$ to time $t_{25}$), the fourth row selection control signal Vsel (4) output from the controlling section 6A to the fourth row selecting wiring $L_{V,4}$ is raised to a high level, thereby closing the respective readout switches $SW_1$ of the N pixels $P_{4,1}$ to $P_{4,N}$ on the fourth row in the photodetecting section 10A.

During the period from time $t_{23}$ to time $t_{24}$ in this period (from time $t_{22}$ to time $t_{25}$), the holding control signal Hold output from the controlling section 6A to the holding wiring $L_H$ is raised to a high level, thereby closing the inputting switches $SW_{31}$ in the N respective holding circuits $H_1$ to $H_N$.

Then, after the period (from time $t_{22}$ to time $t_{25}$), the column selection control signals Hsel (1) to Hsel (N) output from the controlling section 6A to the column selecting wirings $L_{H,1}$ to $L_{H,N}$ are raised to a high level in series only during a given period, thereby closing the outputting switches $SW_{32}$ of the N respective holding circuits $H_1$ to $H_N$ in series only during the given period. As described above, voltage values $V_{out}$ indicating values that the received light intensities in the respective photodiodes PD of the 2N pixels $P_{3,1}$ to $P_{3,N}$ and $P_{4,1}$ to $P_{4,N}$ on the third row and the fourth row are added in the column direction are output to the voltage outputting wiring $L_{out}$.

The voltage values output in series from the N respective holding circuits $H_1$ to $H_N$ are input to the A/D converting section 30, and converted into digital values corresponding to the input voltage values. Then, among the N digital values output from the A/D converting section 30, digital values respectively corresponding to the first row and the second row are added, digital values respectively corresponding to the third row and the fourth row are added, and digital values are added two by two thereafter.

In the first imaging mode, after the operation for the first row and the second row as described above and the following operation for the third row and the fourth row, the same operation for the fifth row to the M-th row is performed thereafter, to obtain frame data showing an image obtained by one-time imaging. Further, when the operation for the M-th row is completed, the same operation is again performed for the range from the first row to the M-th row, to obtain frame data showing a next image. In this way, by repeating the same operation at a constant frequency, voltage values $V_{out}$ indicating two-dimensional intensity distributions in an optical image received by the photodetecting section 10A are output to the voltage outputting wiring $L_{out}$, which enables to repeatedly obtain frame data. Further, a readout pixel pitch in the frame data obtained at this time is made twice as much as a pixel pitch.

Figure 15:
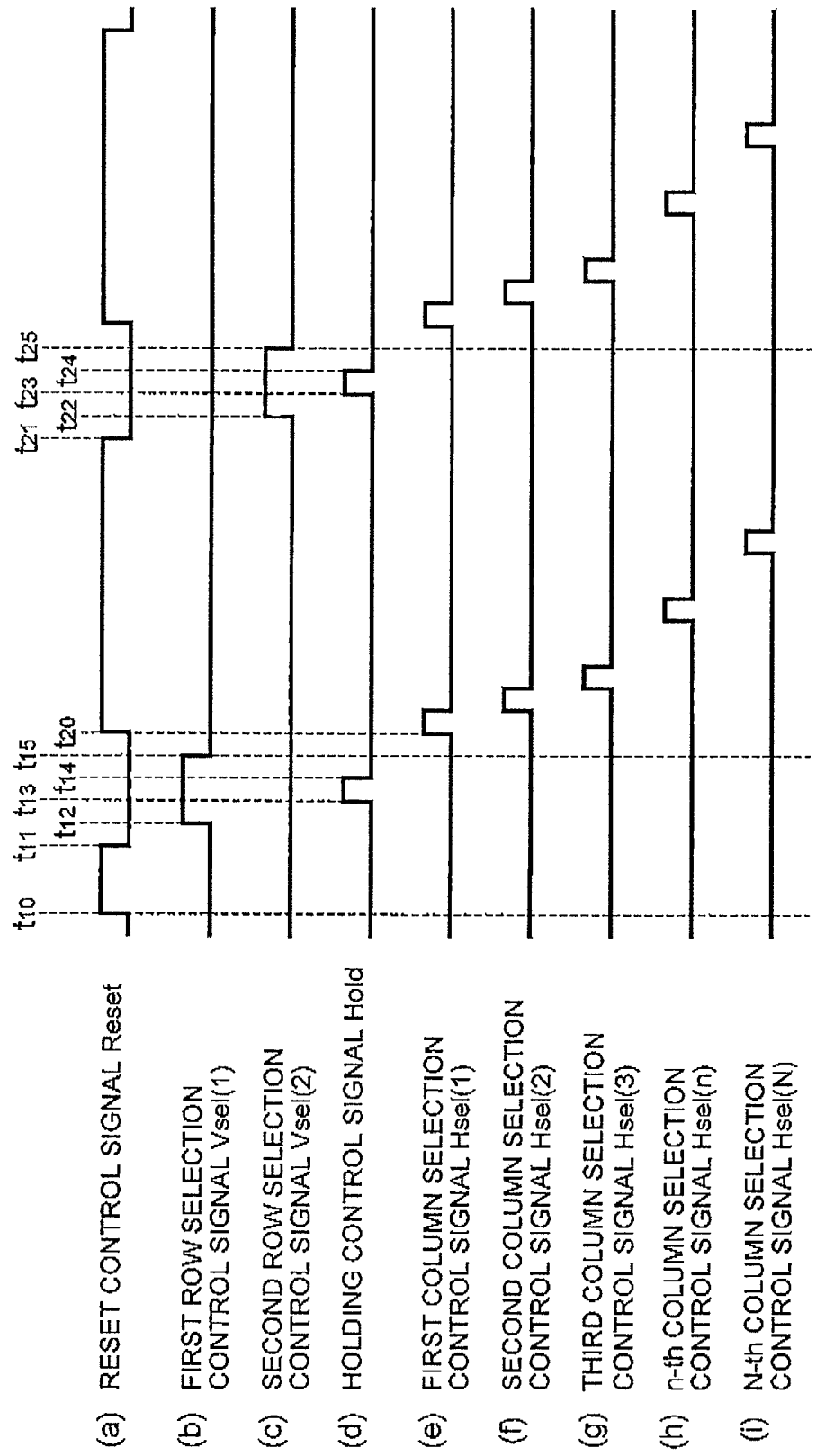
FIG. 15 is a timing chart for explanation of the operation of the solid-state image pickup apparatus 1A according to the first embodiment.
Figure 16:
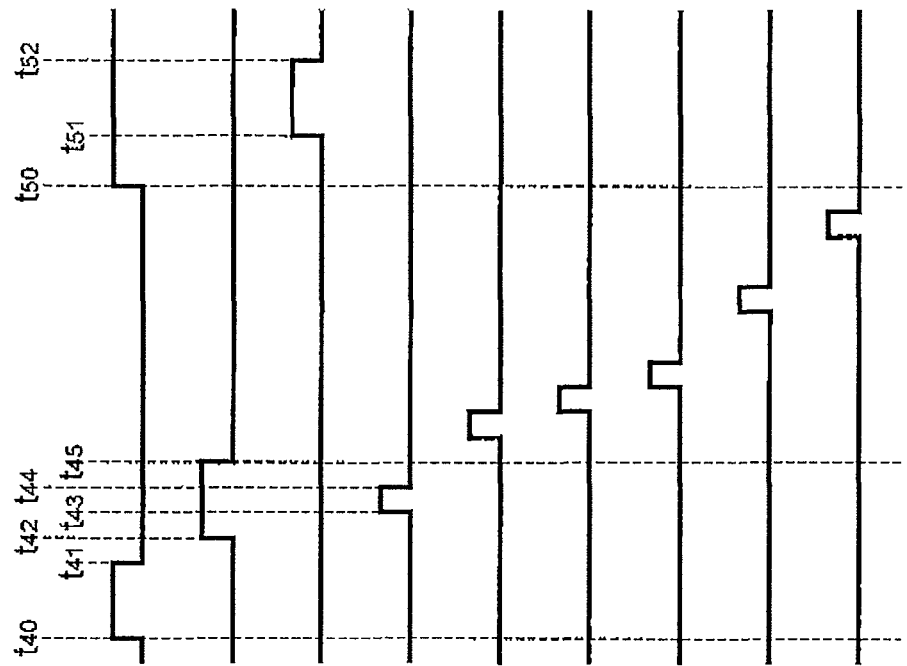
FIG. 16 is a timing chart for explanation of the operation of the solid-state image pickup apparatus 1A according to the first embodiment.

On the other hand, the operation of the solid-state image pickup apparatus 1A in the second imaging mode is as follows. FIG. 15 and FIG. 16 are timing charts for explanation of the operation of the solid-state image pickup apparatus 1A according to the first embodiment. In this second imaging mode, binning-readout is not performed. That is, a readout pixel pitch in frame data is made equal to a pixel pitch. The gain setting switches $SW_{22}$ are open in the respective integrating circuits $S_N$, a capacitance value of the feedback capacitance section is set to a lower value, and a gain is set to a higher value.

FIG. 15 shows the operation for the first row and the second row respectively in the photodetecting section 10A. In this drawing, (a) the reset control signal Reset, (b) the first row selection control signal Vsel (1), (c) the second row selection control signal Vsel (2), (d) the holding control signal Hold, (e) the first column selection control signal Hsel (1), (f) the second column selection control signal Hsel (2), (g) the third column selection control signal Hsel (3), (h) the n-th column selection control signal Hsel (n), and (i) the N-th column selection control signal Hsel (N) are shown in order from the top.

The readout of the charges generated in the respective photodiodes PD of the N pixels $P_{1,1}$ to $P_{1,N}$ on the first row, and accumulated in the junction capacitance section of the photodiodes PD themselves is performed as follows. Before time $t_{10}$, the M row selection control signals Vsel (1) to Vsel (M), the N column selection control signals Hsel (1) to Hsel (N), the reset control signal Reset, and the holding control signal Hold are respectively set to a low level.

During the period from time $t_{10}$ to time $t_{11}$, the reset control signal Reset output from the controlling section 6A to the resetting wiring $L_R$ is raised to a high level, thereby closing the discharging switches $SW_{21}$, and the integral capacitors $C_{21}$ are discharged in the N respective integrating circuits $S_1$ to $S_N$. Further, during the period from time $t_{12}$ to time $t_{15}$ after time $t_{11}$, the first row selection control signal Vsel (1) output from the controlling section 6A to the first row selecting wiring $L_{V,1}$ is raised to a high level, thereby closing the respective readout switches $SW_1$ of the N pixels $P_{1,1}$ to $P_{1,N}$ on the first row in the photodetecting section 10A.

During the period from time $t_{13}$ to time $t_{14}$ in this period (from time $t_{12}$ to time $t_{15}$), the holding control signal Hold output from the controlling section 6A to the holding wiring $L_H$ is raised to a high level, thereby closing the inputting switches $SW_{31}$ in the N respective holding circuits $H_1$ to $H_N$.

During the period (from time $t_{12}$ to time $t_{15}$), the readout switches $SW_1$ of the respective pixels $P_{1,n}$ on the first row are closed, and the discharging switches $SW_{21}$ of the respective integrating circuits $S_n$ are open. Accordingly, the charges generated in the photodiode PD of the pixel $P_{1,n}$ and accumulated in the junction capacitance section of the photodiode PD itself until that moment are transferred to, and to be accumulated in the integral capacitors $C_{21}$ of the integrating circuit $S_n$ via the readout switch $SW_1$ of the pixel $P_{1,n}$ and the n-th column readout wiring $L_{O,n}$. Then, voltage values according to the quantities of charges accumulated in the integral capacitors $C_{21}$ of the respective integrating circuits $S_n$ are output from the output terminals of the integrating circuits $S_n$.

With the holding control signal Hold being shifted from the high level to a low level at time $t_{14}$ in the period (from time $t_{12}$ to time $t_{15}$), the inputting switches $SW_{31}$ are shifted from a closed state to an open state in the N respective holding circuits $H_1$ to $H_N$, and the voltage values output from the output terminals of the integrating circuits $S_n$ at that time to be input to the input terminals of the holding circuits $H_n$ are held in the holding capacitors $C_3$.

Then, after the period (from time $t_{12}$ to time $t_{15}$), the column selection control signals Hsel (1) to Hsel (N) output from the controlling section 6A to the column selecting wirings $L_{H,1}$ to $L_{H,N}$ are raised to a high level in series only during a given period, thereby closing the respective outputting switches $SW_{32}$ of the N holding circuits $H_1$ to $H_N$ in series only during the given period, and the voltage values held in the holding capacitors $C_3$ of the respective holding circuits $H_n$ are output in series to the voltage outputting wiring $L_{out}$ via the outputting switches $SW_{32}$. The voltage values $V_{out}$ output to the voltage outputting wiring $L_{out}$ indicate the received light intensities in the respective photodiodes PD of the N pixels $P_{1,1}$ to $P_{1,N}$ on the first row.

Next, the readout of the charges generated in the respective photodiodes PD of the N pixels $P_{2,1}$ to $P_{2,N}$ on the second row, and accumulated in the junction capacitance sections thereof is performed as follows.

During the period from time $t_{20}$ at which the column selection control signal Hsel (1) is raised to a high level to time $t_{21}$ after the time at which the column selection control signal Hsel (N) is once raised to a high level to be lowered to a low level in the aforementioned operation, the reset control signal Reset output from the controlling section 6A to the resetting wiring $L_R$ is raised to a high level, thereby closing the discharging switches $SW_{21}$, and the integral capacitors $C_{21}$ are discharged in the N respective integrating circuits $S_1$ to $S_N$. Further, during the period from time $t_{22}$ to time $t_{25}$ after time $t_{21}$, the second row selection control signal Vsel (2) output from the controlling section 6A to the second row selecting wiring $L_{V,2}$ is raised to a high level, thereby closing the respective readout switches $SW_1$ of the N pixels $P_{2,1}$ to $P_{2,N}$ on the second row in the photodetecting section 10A.

During the period from time $t_{23}$ to time $t_{24}$ in this period (from time $t_{22}$ to time $t_{25}$), the holding control signal Hold output from the controlling section 6A to the holding wiring $L_H$ is raised to a high level, thereby closing the inputting switches $SW_{31}$ in the N respective holding circuits $H_1$ to $H_N$.

Then, after the period (from time $t_{22}$ to time $t_{25}$), the column selection control signals Hsel (1) to Hsel (N) output from the controlling section 6A to the column selecting wirings $L_{H,1}$ to $L_{H,N}$ are raised to a high level in series only during a given period, thereby closing the respective outputting switches. $SW_{32}$ of the N respective holding circuits $H_1$ to $H_N$ in series only during the given period. As described above, voltage values $V_{out}$ indicating the received light intensities in the respective photodiodes PD of the N pixels $P_{2,1}$ to $P_{2,N}$ on the second row are output to the voltage outputting wiring $L_{out}$.

In the second imaging mode, after the operation for the first row and the second row as described above, the same operation for the third row to the $M_1$-th row is performed, to obtain frame data showing an image obtained by one-time imaging. Further, when the operation for the $M_1$-th row is completed, the same operation is again performed for the range from the first row to the $M_1$-th row to obtain frame data showing a next image. In this way, by repeating the same operation at a constant frequency, voltage values $V_{out}$ indicating two-dimensional intensity distributions in an optical image received by the photodetecting section 10A are output to the voltage outputting wiring $L_{out}$, which enables to repeatedly obtain frame data.

In the second imaging mode, with respect to the range from the $(M_1+1)$-th row to the M-th row, voltage values are not output from the signal readout section 20 to the voltage outputting wiring $L_{out}$. However, with respect to the respective pixels $P_{m,n}$ in the range from the $(M_1+1)$-th row to the M-th row as well, charges generated due to light incidence into the photodiodes PD are accumulated in the junction capacitance sections of the photodiodes PD, and those exceed the saturation level of the junction capacitance sections. When an amount of charges accumulated in the junction capacitance section of the photodiode PD exceeds the saturation level thereof, charges that exceeded the saturation level spill over to the adjacent pixels. Assuming that the adjacent pixels belong to the $M_1$-th row, voltage values of the adjacent pixels output from the signal readout section 20 to the voltage outputting wiring $L_{out}$ are to be inaccurate.

Then, it is preferable that discharge means for discharging the junction capacitance sections of the photodiodes PD of the respective pixels $P_{m,n}$ in the range from the $(M_1+1)$-th row to the M-th row in the second imaging mode is provided. As such discharge means, the solid-state image pickup apparatus 1A according to the present embodiment performs an operation as shown in FIG. 16 in the second imaging mode, to transfer the charges accumulated in the junction capacitance sections of the photodiodes PD of the respective pixels $P_{m,n}$ in the range from the ($M_1$+1)-th row to the M-th row to the integrating circuits $S_n$, which discharges the junction capacitance sections of the photodiodes PD.

FIG. 16 shows the operation for the $M_1$-th row and the ($M_1$+1)-th row respectively in the photodetecting section 10A. In this drawing, (a) the reset control signal Reset, (b) the $M_1$-th row selection control signal Vsel ($M_1$), (c) the ($M_1$+1)-th row selection control signal Vsel ($M_1$+1), (d) the holding control signal Hold, (e) the first column selection control signal Hsel (1), (f) the second column selection control signal Hsel (2), (g) the third column selection control signal Hsel (3), (h) the n-th column selection control signal Hsel (n), and (i) the N-th column selection control signal Hsel (N) are shown in order from the top.

The operation for the $M_1$-th row during the period from time $t_{40}$ to time $t_{50}$ shown in FIG. 16 is the same as the operation for the first row during the period from time $t_{10}$ to time $t_{20}$ shown in FIG. 15. However, during the period from time $t_{42}$ to time $t_{45}$, the $M_1$-th row selection control signal Vsel ($M_1$) output from the controlling section 6A to the $M_1$-th row selecting wiring $L_{V,M1}$ is raised to a high level, thereby closing the respective readout switches $SW_1$ of the N pixels $P_{M1,1}$ to $P_{M1,N}$ on the $M_1$-th row in the photodetecting section 10A.

In the second imaging mode, when the operation for the $M_1$-th row is completed, the operation for the range from the ($M_1$+1)-th row to the M-th row is performed on and after time $t_{50}$. That is, on and after time $t_{50}$, the reset control signal Reset output from the controlling section 6A to the resetting wiring $L_R$ is raised to a high level, thereby closing the discharging switches $SW_{21}$ in the N respective integrating circuits $S_1$ to $S_N$. Further, during the period in which the discharging switches $SW_{21}$ are closed on and after time $t_{50}$, the ($M_1$+1)-th to M-th row selection control signals Vsel ($M_1$+1) to Vsel (M) are raised to a high level, thereby closing the respective readout switches $SW_1$ of the respective pixels $P_{m,n}$ in the range from the ($M_1$+1)-th row to the M-th row in the photodetecting section 10A.

In this way, in the second imaging mode, when the readout switches $SW_1$ of the respective pixels $P_{m,n}$ in the range from the ($M_1$+1)-th row to the M-th row are closed, the charges accumulated in the junction capacitance sections of the photodiodes PD of the pixels are transferred to the integrating circuits $S_n$, and further, with the discharging switches $SW_{21}$ being closed in the respective integrating circuits $S_n$, the integral capacitors $C_{21}$ of the respective integrating circuits $S_n$ are to be always discharged. In this way, in the second imaging mode, it is possible to discharge the junction capacitance sections of the photodiodes PD of the respective pixels $P_{m,n}$ in the range from the ($M_1$+1)-th row to the M-th row.

At this time, with respect to the range from the ($M_1$+1)-th row to the M-th row, the row selection control signals Vsel ($M_1$+1) to Vsel (M) may be raised to a high level in series. However, a plurality of row selection control signals among the row selection control signals Vsel ($M_1$+1) to Vsel (M) may be simultaneously raised to a high level, and all the row selection control signals Vsel ($M_1$+1) to Vsel (M) may be simultaneously raised to a high level. In this way, with respect to the range from the ($M_1$+1)-th row to the M-th row, provided that a plurality or all of the row selection control signals are simultaneously raised to a high level, it is possible to discharge the junction capacitance sections of the photodiodes PD of the respective pixels $P_{m,n}$ in a shorter period of time.

Meanwhile, as another imaging mode in which the number of pieces of data of pixels which are less than those in the first imaging mode are output from the signal readout section 20, voltage values corresponding to the quantities of charges generated in the photodiodes PD of the respective pixels $P_{m,n}$ included in successive $N_1$ columns in the photodetecting section 10A may be output from the signal readout section 20. Here, $N_1$ is an integer less than N. However, in such an imaging mode in which the data of the respective pixels $P_{m,n}$ on the $N_1$ columns are output from the signal readout section 20, it is necessary to output the M row selection control signals Vsel (1) to Vsel (M) from the controlling section 6A in order to obtain one frame data. In contrast thereto, in the solid-state image pickup apparatus 1A according to the present embodiment, in the second imaging mode in which the data of the respective pixels $P_{m,n}$ on the $M_1$ rows are output from the signal readout section 20, it suffices to output the $M_1$ row selection control signals Vsel (1) to Vsel ($M_1$) from the controlling section 6A in order to obtain one frame data, therefore, it is possible to perform a high-speed operation.

Further, in order to read out pixel data at a higher speed, the signal readout section 20 and the A/D converting section 30 in the above-described embodiment are divided into a plurality of sets, and pixel data may be output concurrently from the respective sets.

Figure 17:
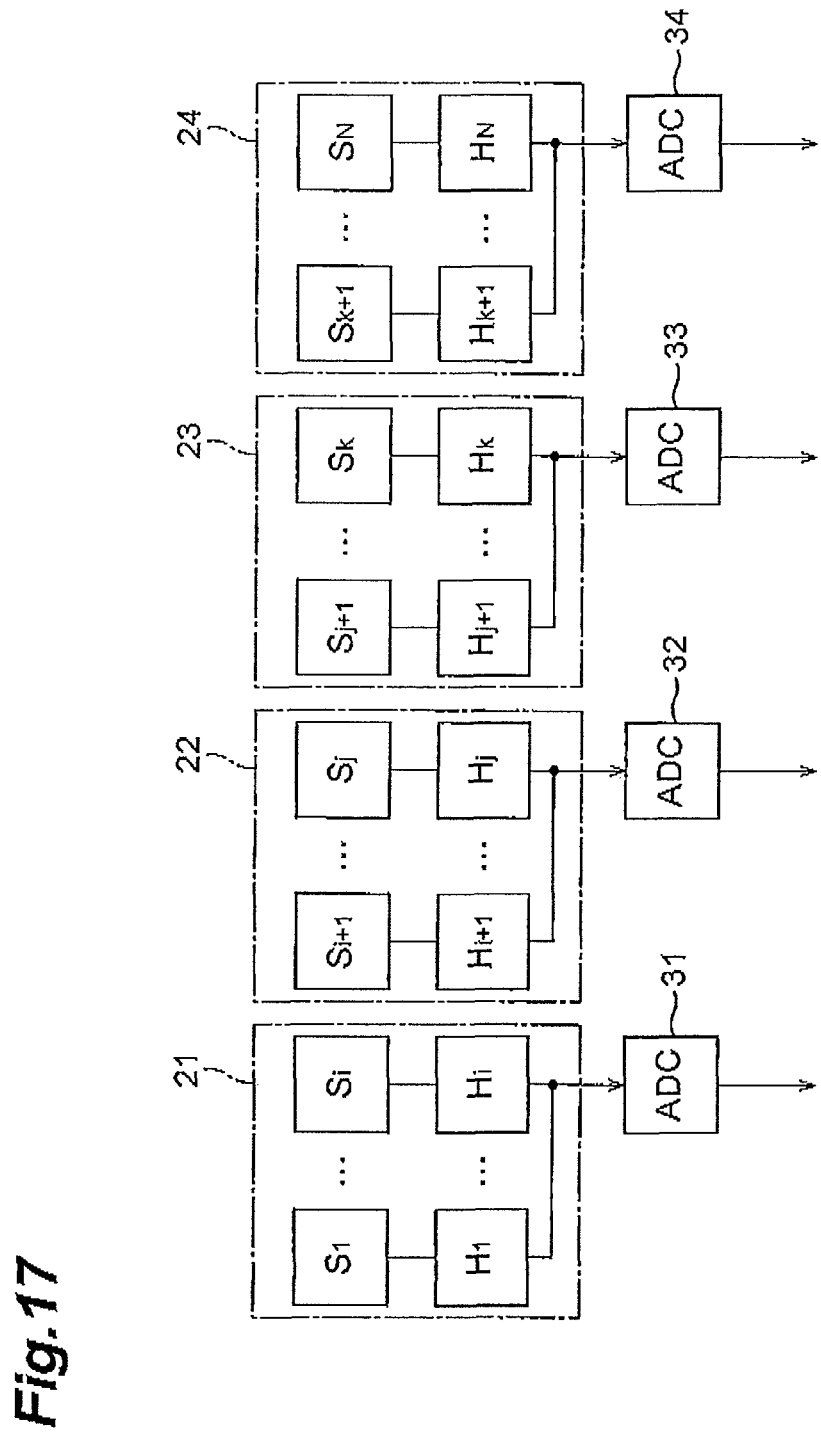
FIG. 17 is a diagram showing a modification of the configuration of the solid-state image pickup apparatus 1A according to the first embodiment.

For example, as shown in FIG. 17, the N integrating circuits $S_1$ to $S_N$ and the N holding circuits $H_1$ to $H_N$ are divided into four sets, and a signal readout section 21 composed of the integrating circuits $S_1$ to $S_i$ and the holding circuits $H_1$ to $H_i$ is defined as the first set, a signal readout section 22 composed of the integrating circuits $S_{i+1}$ to $S_j$ and the holding circuits $H_{i+1}$ to $H_j$ is defined as the second set, a signal readout section 23 composed of the integrating circuits $S_{j+1}$ to $S_k$ and the holding circuits $H_{j+1}$ to $H_k$ is defined as the third set, and a signal readout section 24 composed of the integrating circuits $S_{k+1}$ to $S_N$ and the holding circuits $H_{k+1}$ to $H_N$ is defined as the fourth set. Here, "1<i<j<k<N". Then, voltage values output in series from the respective holding circuits $H_1$ to $H_i$ of the signal readout section 21 are converted into digital values by an A/D converting section 31, voltage values output in series from the respective holding circuits $H_{i+1}$ to $H_j$ of the signal readout section 22 are converted into digital values by an A/D converting section 32, voltage values output in series from the respective holding circuits $H_{j+1}$ to $H_k$ of the signal readout section 23 are converted into digital values by an A/D converting section 33, and voltage values output in series from the respective holding circuits $H_{k+1}$ to $H_N$ of the signal readout section 24 are converted into digital values by an A/D converting section 34. Further, analog-to-digital conversion processing in the four respective A/D converting sections 31 to 34 is performed concurrently. In this way, it is possible to read out pixel data at a higher speed.

Further, considering that binning-readout of two rows and two columns is performed, it is also preferable that the holding circuits corresponding to the odd-number columns among the N holding circuits $H_1$ to $H_N$ are defined as the first set, the holding circuits corresponding to the even-number columns are defined as the second set, and A/D converting sections are separately provided to the first and second respective sets, and these two A/D converting sections are operated concurrently. In this case, voltage values are simultaneously output from the holding circuits corresponding to the odd-number columns and the holding circuits corresponding to the even-number columns, and analog-to-digital conversion processing is simultaneously carried out with respect to these two voltage values into digital values. Then, at the time of binning processing, these two digital values are added. In this way as well, it is possible to read out pixel data at a high speed.

In addition, with respect to scanning processing in the column direction by the scanning shift register 40, division as described above is impossible. This is because it is necessary to perform scanning from the first pixel to the last pixel in series in scanning processing of the column direction. Since the number of columns N is greater than the number of rows M in the solid-state image pickup apparatus 1A according to the present embodiment, it is possible to more significantly have the effect of accelerating readout by dividing the signal readout section as described above.

Figure 18:
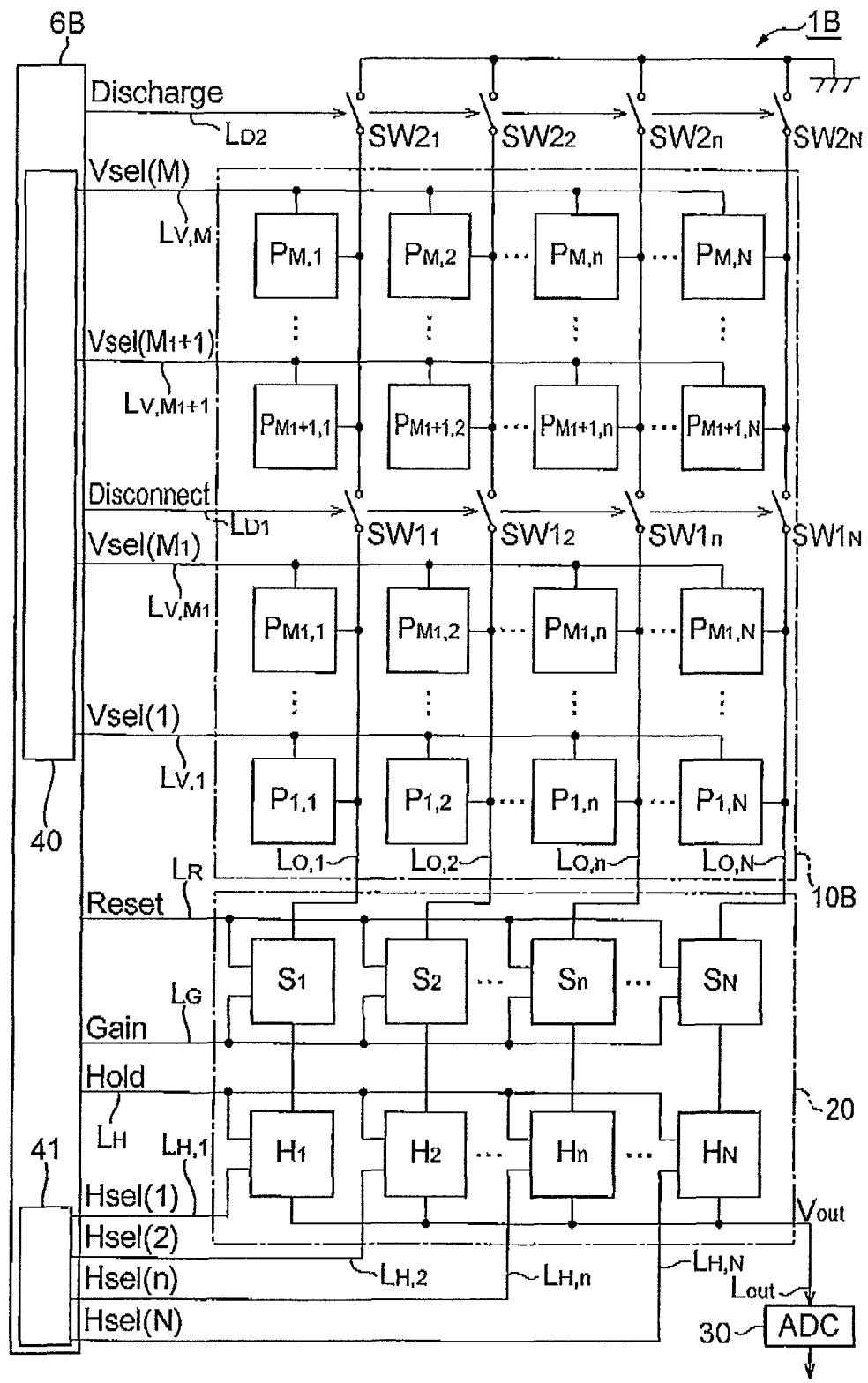
FIG. 18 is a diagram showing the configuration of a solid-state image pickup apparatus 1B according to a second embodiment.

Next, a solid-state image pickup apparatus 1B according to a second embodiment will be described. FIG. 18 is a diagram showing a configuration of the solid-state image pickup apparatus 1B according to the second embodiment. The solid-state image pickup apparatus 1B shown in this drawing is equipped with a photodetecting section 10B, the signal readout section 20, the A/D converting section 30, and a controlling section 6B. Further, a scintillator (not shown) is provided so as to cover the photodetecting section 10B of the solid-state image pickup apparatus 1B.

As compared with the configuration of the solid-state image pickup apparatus 1A according to the first embodiment shown in FIG. 11, the solid-state image pickup apparatus 1B according to the second embodiment shown in this FIG. 18 is different in the point that disconnecting switches $SW1_n$ and discharging switch $SW2_n$ are provided on the respective n-th column readout wirings $L_{O, n}$, and also in the point that the controlling section 6B is equipped in place of the controlling section 6A.

The respective disconnecting switches $SW1_n$ are provided on the readout wirings $L_{O, n}$, and between the $M_1$-th row and the $(M_1+1)$-th row in the photodetecting section 6B. That is, when the disconnecting switches $SW1_n$ are closed, the respective pixels $P_{m, n}$ in the range from the first row to the M-th row are connected to the signal readout section 20 via the readout wirings $L_{O, n}$. On the other hand, when the disconnecting switches $SW1_n$ are open, although the respective pixels $P_{m, n}$ in the range from the first row to the $M_1$-th row are connected to the signal readout section 20 via the readout wirings $L_{O, n}$, the respective pixels $P_{m, n}$ in the range from the $(M_1+1)$-th row to the M-th row are disconnected from the signal readout section 20. The respective disconnecting switches $SW1_n$ are connected to the controlling section 10B via a disconnecting wiring $L_{D1}$, and a disconnection control signal Disconnect passing through the disconnecting wiring $L_{D1}$ from the controlling section 6B is provided to the respective disconnecting switches $SW1_n$. The disconnection control signal Disconnect is for instructing switching operations of the respective disconnecting switches $SW1_n$.

The respective discharging switches $SW2_n$ are provided on the readout wirings $L_{O, n}$, and on the side farther away from the signal readout section 20 than the positions at which the disconnecting switches SW1n are provided. Ends on one side of the discharging switches $SW2_n$ are connected to the respective pixels $P_{m, n}$ in the range from the $(M_1+1)$-th row to the M-th row via the readout wirings $L_{O, n}$. Ends on the other side of the discharging switches $SW2_n$ are grounded. The respective discharging switches $SW2_n$ are connected to the controlling section 6B via a discharging wiring $L_{D2}$, and a discharge control signal Discharge passing through the discharging wiring $L_{D2}$ from the controlling section 6B is provided to the respective discharging switches $SW2_n$. The discharge control signal Discharge is for instructing switching operations of the respective discharging switches $SW2_n$.

In the same way as the controlling section 6A in the first embodiment, the controlling section 6B outputs a reset control signal Reset to the resetting wiring $L_R$, outputs a gain setting signal Gain to the gain setting wiring $L_G$, and outputs a holding control signal Hold to the holding wiring $L_H$. The scanning shift register 40 of the controlling section 6B outputs an m-th row selection control signal Vsel (m) to an m-th row selecting wirings $L_{V, m}$. The readout shift register 41 of the controlling section 6B outputs an n-th column selection control signal Hsel (n) to an n-th column selecting wiring $L_{H, n}$.

Additionally, the controlling section 6B outputs a disconnection control signal Disconnect to the disconnecting wiring $L_{D1}$, to provide the disconnection control signal Disconnect to the N respective disconnecting switches $SW1_1$ to $SW1_N$. Further, the controlling section 6B outputs a discharge control, signal Discharge to the disconnecting wiring $L_{D2}$, to provide the discharge control signal Discharge to the N respective discharging switches $SW2_1$ to $SW2_N$.

The solid-state image pickup apparatus 1B according to the second embodiment as well has a first imaging mode and a second imaging mode. The imaging areas in the photodetecting section 10B in the first imaging mode and the second imaging mode are different from each other. The controlling section 6B outputs voltage values corresponding to the quantities of charges generated in the respective photodiodes PD of the M×N pixels $P_{1, 1}$ to $P_{M, N}$ in the photodetecting section 10B from the signal readout section 20 in the first imaging mode. Further, the controlling section 6B outputs voltage values corresponding to the quantities of charges generated in the photodiodes PD of the respective pixels $P_{m, n}$ in the range from the first row to the $M_1$-th row in the photodetecting section 10B from the signal readout section 20 in the second imaging mode.

Further, in the second imaging mode, the controlling section 6B reduces a readout pixel pitch in frame data based on a voltage value output from the signal readout section 20 as compared to the first imaging mode, raises a frame rate, that is the number of pieces of frame data to be output per unit time, and increases gain, that is a ratio of an output voltage value to an amount of input charges in the signal readout section 20.

In the solid-state image pickup apparatus 1B according to the second embodiment, in the first imaging mode, the disconnection control signal Disconnect provided to the respective disconnecting switches $SW1_n$ via the disconnecting wiring $L_{D1}$ from the controlling section 6B is raised to a high level, and the respective disconnecting switches $SW1_n$ are closed. Further, the discharge control signal Discharge provided to the respective discharging switches $SW2_n$ via the discharging wiring $L_{D2}$ from the controlling section 6B is lowered to a low level, and the respective discharging switches $SW2_n$ are opened. In this state, the respective pixels $P_{m, n}$ in the range from the first row to the M-th row are connected to the signal readout section 20 via the readout wirings $L_{O, n}$. Then, the same operation as in the case of the first embodiment is performed, to discharge voltage values corresponding to the quantities of charges generated in the respective photodiodes PD of the M×N pixels $P_{1, 1}$ to $P_{M, N}$ in the photodetecting section 10B from the signal readout section 20.

On the other hand, in the solid-state image pickup apparatus 1B according to the second embodiment, in the second imaging mode, the disconnection control signal Disconnect provided to the respective disconnecting switches $SW1_n$ via the disconnecting wiring $L_{D1}$ from the controlling section 6B is lowered to a low level, and the respective disconnecting switches $SW1_n$ are opened. Further, the discharge control signal Discharge provided to the respective discharging switches $SW2_n$ via the discharging wiring $L_{D2}$ from the controlling section 6B is raised to a high level, and the respective discharging switches $SW2_n$ are closed. In this state, the respective pixels $P_{m,n}$ in the range from the first row to the M-th row are connected to the signal readout section 20 via the readout wirings $L_{O,n}$. However, the respective pixels $P_{m,n}$ in the range from the $(H_1+1)$-th row to the M-th row are disconnected from the signal readout section 20, to be grounded.

Then, in the second imaging mode, with respect to the range from the first row to the $M_1$-th row, the same operation as in the case of the first embodiment is performed, to output voltage values corresponding to the quantities of charges generated in the photodiodes PD of the respective pixels from the signal readout section 20. On the other hand, with respect to the range from the $(M_1+1)$-th row to the M-th row, the row selection control signals Vsel $(M_1+1)$ to Vsel (M) are raised to a high level, thereby making the cathode terminals of the photodiodes PD of the respective pixels $P_{m,n}$ be grounded via the readout switches $SW1_n$ and the discharging switches $SW2_n$, and therefore, the junction capacitance sections of the photodiodes PD of the respective pixels $P_{m,n}$ are discharged. That is, in this case, the respective discharging switches $SW2_n$ serve as discharge means for discharging the junction capacitance sections of the photodiodes PD of the respective pixels $P_{m,n}$ in the range from the $(M_1+1)$-th row to the M-th row in the second imaging mode.

In the second imaging mode, with respect to the range from the $(M_1+1)$-th row to the M-throw, the row selection control signals Vsel $(M_1+1)$ to Vsel (M) may be raised to a high level in series. However, a plurality of row selection control signals among the row selection control signals Vsel $(M_1+1)$ to Vsel (M) may be simultaneously raised to a high level, and all the row selection control signals Vsel $(M_1+1)$ to Vsel (M) may be simultaneously raised to a high level. In this way, with respect to the range from the $(M_1+1)$-th row to the M-th row, provided that a plurality or all of the row selection control signals are simultaneously raised to a high level, it is possible to discharge the junction capacitance sections of the photodiodes PD of the respective pixels $P_{m,n}$ in a shorter period of time.

Further, in the second imaging mode, the period in which voltage values corresponding to the quantities of charges generated in the photodiodes PD of the respective pixels $P_{m,n}$ in the range from the first row to the $M_1$-th row are output from the signal readout section 20 and the period in which the junction capacitance sections of the photodiodes PD of the respective pixels $P_{m,n}$ in the range from the $(M_1+1)$-th row to the M-th row may be partially overlapped each other. In such a case, a higher-speed operation is possible.

Further, in the second imaging mode, the n-th column readout wirings $L_{O,n}$ connected to the signal readout section 20 are shortened due to the disconnecting wiring $L_{D1}$ being opened, which makes it possible to reduce noise.

The X-ray image pickup system for medical use according to the present invention is not limited to the above-described embodiments, and other various modifications are possible. For example, in the first embodiment, the imaging area composed of the pixels on the successive $M_1$ rows ($M_1<M$) among the pixels arrayed on the M rows is exemplified as an imaging area in the second imaging mode. However, an imaging area in the second imaging mode may be an area other than this imaging area, or the entire surface of the photodetecting section may be used as an imaging area. Further, the first imaging mode as well is not limited to the form in which the entire surface of the photodetecting section is used as an imaging area as in the above-described embodiment, and any arbitrary area in the photodetecting section may be used as an imaging area as necessary.

INDUSTRIAL APPLICABILITY

The present invention can be utilized for an X-ray image pickup system for medical use.

REFERENCE SIGNS LIST 1A, 1B Solid-state image pickup apparatuses
3 Semiconductor substrate
4 Scintillator
5 X-ray shielding section
6A, 6B Controlling sections
10A, 10B, 110, 130 Photodetecting sections
10a, 10b Imaging areas
11 Photosensitive surface
20, 120, 140 Signal readout sections
30, 31 to 34 A/D converting sections
40 Scanning shift register
41 Readout shift register
100 X-ray image pickup system
104 Swivel arm
106 X-ray generator
108 Rotation controlling section
A Subject
$A_2$ Amplifier
$C_{21}$, $C_{22}$ Integral capacitors
$C_3$ Holding capacitor
$H_1$ to $H_N$ Holding circuits
$L_G$ Gain setting wiring
$L_H$ Holding wiring
$L_{H,n}$ n-th column selecting wiring
$L_{O,n}$ n-th column readout wiring
$L_{out}$ Voltage outputting wiring
$L_R$ Resetting wiring
$L_{v,m}$ m-th row selecting wiring
P, $P_{m,n}$ Pixels
Reset Reset control signal
$S_1$ to $S_N$ Integrating circuits
$SW_1$ Readout switch
$SW_{21}$ Discharging switch
$SW_{22}$ Gain setting switch
$SW_{31}$ Inputting switch
$SW_{32}$ Outputting switch
$SW1_1$ to $SW1_N$ Disconnecting switches
$SW2_1$ to $SW2_N$ Discharging switches
W Silicon wafer

The invention claimed is:

1. An X-ray image pickup system for medical use which has at least two imaging modes, comprising a solid-state image pickup apparatus, where M<N and M and N are integers greater than or equal to 2, which takes an X-ray image while moving around a jaw portion of a test subject, wherein, the solid-state image pickup apparatus has a photodetecting section which is formed such that M×N pixels respectively including photodiodes are two-dimensionally arrayed in M rows and N columns, the photodetecting section has a rectangular photosensitive surface whose longitudinal direction is the row direction, N readout wirings which are installed on the respective columns, and connected to the photodiodes included in the pixels on corresponding columns via readout switches, a signal readout section which holds voltage values corresponding to quantities of charges input via the readout wirings, and outputs the holding voltage values in series, a controlling section which controls switching operations of the readout switches of the respective pixels, and controls outputting operations of voltage values in the signal readout section, to output the voltage values corresponding to the quantities of charges generated in the photodiodes of the respective pixels from the signal readout section, and a scintillator which generates a scintillation light according to an incident X-ray to convert the X-ray image into an optical image, and outputs the optical image to the photodetecting section, the X-ray image pickup system for medical use further comprises a rotation controlling section which supports the solid-state image pickup apparatus rotatably around an axis line vertical to the photosensitive surface, and controls a rotation angle of the solid-state image pickup apparatus such that the longitudinal direction of the photodetecting section is made parallel to a moving direction of the solid-state image pickup apparatus in one imaging mode of the two imaging modes, and the longitudinal direction of the photodetecting section is made perpendicular to the moving direction of the solid-state image pickup apparatus in the other imaging mode of the two imaging modes.

2. The X-ray image pickup system for medical use according to claim 1, wherein,
a rotation center of the solid-state image pickup apparatus is located at one corner of the four corners of the rectangular photo detecting section, and
the solid-state image pickup apparatus is rotated such that the one corner is located on the lower jaw side of the test subject in both of the two imaging modes.

3. The X-ray image pickup system for medical use according to claim 1, wherein,
the controlling section outputs voltage values corresponding to the quantities of charges generated in the photodiodes of the M×N respective pixels in the photo detecting section from the signal readout section in the one imaging mode, and
the controlling section outputs voltage values corresponding to the quantities of charges generated in the photodiodes of the respective pixels included in a specific range of successive $M_1$ rows ($M_1<M$) in the photodetecting section from the signal readout section in the other imaging mode.

4. The X-ray image pickup system for medical use according to claim 3, wherein,
in the other imaging mode, the controlling section sets a range of $M_1$ rows counted in order from the row closest to the signal readout section among the M rows in the photodetecting section as the specific range, and outputs voltage values corresponding to the quantities of charges generated in the photodiodes of the respective pixels in the specific range.

5. The X-ray image pickup system for medical use according to claim 4, wherein,
the solid-state image pickup apparatus further has disconnecting switches which are provided on the respective readout wirings between the specific range in the photodetecting section and the other range except for the specific range, and
the controlling section closes the disconnecting switches in the one imaging mode, and opens the disconnecting switches in the other imaging mode.

6. The X-ray image pickup system for medical use according to claim 3, wherein,
the solid-state image pickup apparatus further has discharge means for discharging junction capacitance sections of the photodiodes of the respective pixels in the other range except for the specific range in the photodetecting section in the other imaging mode.

7. The X-ray image pickup system for medical use according to claim 1, wherein,
in the other imaging mode, the controlling section reduces a readout pixel pitch in frame data based on a voltage value output from the signal readout section as compared to the one imaging mode, speeds up a frame rate, that is the number of pieces of frame data to be output per unit time, and increases gain, that is a ratio of an output voltage value to an amount of input charges in the signal readout section.

8. The X-ray image pickup system for medical use according to claim 1, wherein,
the one imaging mode is an imaging mode for carrying out CT scan in dental X-ray photography, and the other imaging mode is an imaging mode for carrying out panoramic radiography in dental X-ray photography.

9. An X-ray image pickup system for medical use which has at least two imaging modes, comprising a solid-state image pickup apparatus, where M<N and M and N are integers greater than or equal to 2, which takes an X-ray image while moving around a jaw portion of a test subject, wherein,
the solid-state image pickup apparatus has a photodetecting section which is formed such that M×N pixels respectively including photodiodes are two-dimensionally arrayed in M rows and N columns, the photodetecting section has a rectangular photosensitive surface whose longitudinal direction is the row direction, N readout wirings which are installed on the respective columns, and connected to the photodiodes included in the pixels on corresponding columns via readout switches, a signal readout section connected to the readout wiring, wherein the signal readout section holds voltage values corresponding to quantities of charges accumulated in the photodiode, and outputs the holding voltage values in series, a controlling section which controls switching operations of the readout switches of the respective pixels, and controls outputting operations of voltage values in the signal readout section, to output the voltage values corresponding to the quantities of charges generated in the photodiodes of the respective pixels from the signal readout section, and a scintillator which generates a scintillation light according to an incident X-ray to convert the X-ray image into an optical image, and outputs the optical image to the photodetecting section, the X-ray image pickup system for medical use further comprises a rotation controlling section which supports the solid-state image pickup apparatus rotatably around an axis line vertical to the photosensitive surface, and controls a rotation angle of the solid-state image pickup apparatus such that the longitudinal direction of the photodetecting section is made parallel to a moving direction of the solid-state image pickup apparatus in one imaging mode of the two imaging modes, and the longitudinal direction of the photodetecting section is made perpendicular to the moving direction of the solid-state image pickup apparatus in the other imaging mode of the two imaging modes.

10. An X-ray image pickup system for medical use which has at least two imaging modes, comprising a solid-state image pickup apparatus, where M<N and M and N are integers greater than or equal to 2, which takes an X-ray image while moving around a jaw portion of a test subject, wherein, the solid-state image pickup apparatus has a photodetecting section which is formed such that M×N pixels respectively including photodiodes are two-dimensionally arrayed in M rows and N columns, the photodetecting section has a rectangular photosensitive surface whose longitudinal direction is the row direction, N readout wirings which are installed on the respective columns, and connected to the photodiodes included in the pixels on corresponding columns via readout switches, a signal readout section connected to the readout wiring, wherein the signal readout section holds values corresponding to quantities of charges accumulated in the photodiode, and outputs the holding values in series, a controlling section which controls switching operations of the readout switches of the respective pixels, and controls outputting operations of values in the signal readout section, to output the values corresponding to the quantities of charges generated in the photodiodes of the respective pixels from the signal readout section, and a scintillator which generates a scintillation light according to an incident X-ray to convert the X-ray image into an optical image, and outputs the optical image to the photodetecting section, the X-ray image pickup system for medical use further comprises a rotation controlling section which supports the solid-state image pickup apparatus rotatably around an axis line vertical to the photosensitive surface, and controls a rotation angle of the solid-state image pickup apparatus such that the longitudinal direction of the photodetecting section is made parallel to a moving direction of the solid-state image pickup apparatus in one imaging mode of the two imaging modes, and the longitudinal direction of the photodetecting section is made perpendicular to the moving direction of the solid-state image pickup apparatus in the other imaging mode of the two imaging modes.

11. An X-ray image pickup system for medical use, comprising a solid-state image pickup apparatus,
where
M<N and
M and N are integers greater than or equal to 2,
which takes an X-ray image while moving around a jaw portion of a test subject, wherein,
the solid-state image pickup apparatus has a photodetecting section which is formed such that M×N pixels respectively including photodiodes are two-dimensionally arrayed in M rows and N columns, the photodetecting section has a rectangular photosensitive surface whose longitudinal direction is the row direction,
N readout wirings which are installed on the respective columns, and connected to the photodiodes included in the pixels on corresponding columns via readout switches,
a signal readout section arranged along the longitudinal direction of the photodetecting section,
  wherein the signal readout section includes N holding circuits $H_1$ to $H_N$,
  wherein the holding circuits are connected to the respective readout wirings,
  wherein each of the holding circuits hold a value,
  wherein each of the values is corresponding to amount of charges generated in each of the photodiodes and
  wherein the respective holding circuits output the holding values in series,
a controlling section which controls switching operations of the readout switches of the respective pixels, and controls outputting operations of values in the signal readout section, to output the values corresponding to the quantities of charges generated in the photodiodes of the respective pixels from the signal readout section, and
the X-ray image pickup system for medical use further comprises the longitudinal direction of the photodetecting section is made perpendicular to the moving direction of the solid-state image pickup apparatus in a predetermined imaging mode.

12. The X-ray image pickup system according to claim 11, wherein
the size of the photodetecting section in the row direction is 15 cm or more, and
the size of the photodetecting section in the column direction is 7 mm or more.

13. The X-ray image pickup system according to claim 11 comprising a function of a panoramic radiography imaging mode.

14. The X-ray image pickup system according to claim 11 comprising a function of a cephalometrical radiography imaging mode.

15. The X-ray image pickup system according to claim 11, wherein the signal readout section comprises a plurality of amplifiers provided for the respective columns.

16. The X-ray image pickup system according to claim 11, wherein said value is a voltage value.

17. An X-ray image pickup system for medical use, comprising a solid-state image pickup apparatus,
where
M<N and
M and N are integers greater than or equal to 2,
which takes an X-ray image while moving around a jaw portion of a test subject, wherein,
the solid-state image pickup apparatus has a detector which is formed such that M×N pixels are two-dimensionally arrayed in M rows and N columns,
N readout wirings which are installed on the respective columns, and connected to the pixels on corresponding columns via readout switches,
a signal readout section arranged along the longitudinal direction of the detector,
  wherein the signal readout section includes N holding circuits H1 to HN,
  wherein the holding circuits are connected to the respective readout wirings,
  wherein each of the holding circuits hold a value,
  wherein each of the values is corresponding to amount of charges generated in each of the pixels and
  wherein the respective holding circuits output the holding values in series,
a controlling section which controls switching operations of the readout switches of the respective pixels, and controls outputting operations of values in the signal readout section, to output the values corresponding to the quantities of charges generated in the respective pixels from the signal readout section, and
the X-ray image pickup system for medical use further comprises the longitudinal direction of the detector is made perpendicular to the moving direction of the solid-state image pickup apparatus in a predetermined imaging mode.

\* \* \* \* \*